US011612449B2

(12) United States Patent
Furutani et al.

(10) Patent No.: US 11,612,449 B2
(45) Date of Patent: Mar. 28, 2023

(54) WEARABLE PATCH, AND SHEET-TYPE CELL

(71) Applicant: Maxell, Ltd., Kyoto (JP)

(72) Inventors: Takahiro Furutani, Kyoto (JP); Mitsutoshi Watanabe, Kyoto (JP); Hiroaki Ono, Kyoto (JP)

(73) Assignee: Maxell, Ltd., Kyoto (JP)

( * ) Notice: Subject to any disclaimer, the term of this patent is extended or adjusted under 35 U.S.C. 154(b) by 937 days.

(21) Appl. No.: 16/475,975

(22) PCT Filed: Jan. 5, 2018

(86) PCT No.: PCT/JP2018/000073
§ 371 (c)(1),
(2) Date: Jul. 3, 2019

(87) PCT Pub. No.: WO2018/128191
PCT Pub. Date: Jul. 12, 2018

(65) Prior Publication Data
US 2019/0350665 A1    Nov. 21, 2019

(30) Foreign Application Priority Data

Jan. 5, 2017   (JP) .............................. JP2017-000392
Oct. 30, 2017  (JP) .............................. JP2017-209560

(51) Int. Cl.
*A61B 90/00*   (2016.01)
*H01M 50/557*  (2021.01)
(Continued)

(52) U.S. Cl.
CPC .............. *A61B 90/08* (2016.02); *A61B 5/103* (2013.01); *H01M 50/557* (2021.01); *A61B 5/01* (2013.01);
(Continued)

(58) Field of Classification Search
CPC ...... A61B 90/08; A61B 5/103; H01M 50/572; H01M 50/557
See application file for complete search history.

(56) References Cited

U.S. PATENT DOCUMENTS

2007/0123756 A1* 5/2007 Kitajima ............ A61B 5/14552
600/595
2014/0121557 A1   5/2014 Gannon et al.
2016/0360991 A1  12/2016 Kubota et al.

FOREIGN PATENT DOCUMENTS

JP   2004-252171 A    9/2004
JP   2006-351431 A   12/2006
(Continued)

OTHER PUBLICATIONS

Extended European Search Report, dated Jul. 27, 2020, for European Application No. 18735941.9.
(Continued)

*Primary Examiner* — Curtis B Odom
(74) *Attorney, Agent, or Firm* — Birch, Stewart, Kolasch & Birch, LLP

(57) ABSTRACT

Provided is a wearable patch that can reliably interrupt the power supply from the cell after use and can be disposed of as it is. Moreover, provided is a sheet-type cell that can reliably interrupt the power supply after use and can be disposed of safely. The wearable patch is worn on the body and includes a functional element, a drive circuit unit that operates the functional element, and a cell as a power source. A cutting facilitating member is formed to allow a predetermined portion of the wearable patch to be cut with a force of 200 N or less so that the power supply from the cell to the drive circuit unit is interrupted.

17 Claims, 10 Drawing Sheets

(51) Int. Cl.
*A61B 5/103* (2006.01)
*A61B 5/01* (2006.01)
*A61B 5/024* (2006.01)
*A61B 5/00* (2006.01)
*A61M 37/00* (2006.01)
*H01M 50/119* (2021.01)
*H01M 50/133* (2021.01)
*H01M 50/121* (2021.01)
*H01M 50/124* (2021.01)
*H01M 50/593* (2021.01)

(52) U.S. Cl.
CPC ......... *A61B 5/02438* (2013.01); *A61B 5/6833* (2013.01); *A61B 2090/037* (2016.02); *A61B 2560/0214* (2013.01); *A61M 37/00* (2013.01); *H01M 50/119* (2021.01); *H01M 50/121* (2021.01); *H01M 50/124* (2021.01); *H01M 50/133* (2021.01); *H01M 50/593* (2021.01)

(56) References Cited

FOREIGN PATENT DOCUMENTS

| | | |
|---|---|---|
| JP | 2007-105316 A | 4/2007 |
| JP | 2008-516248 A | 5/2008 |
| JP | 2016-505808 A | 2/2016 |
| JP | 2016-515022 A | 5/2016 |
| JP | 2017-000370 A | 1/2017 |
| WO | WO 2006/040106 A1 | 4/2006 |
| WO | WO 2014/070254 A1 | 5/2014 |
| WO | WO 2014/165071 A1 | 10/2014 |

OTHER PUBLICATIONS

International Search Report for PCT/JP2018/000073 (PCT/ISA/210) dated Apr. 3, 2018, with English translation.

* cited by examiner

WEARABLE PATCH, AND SHEET-TYPE CELL

TECHNICAL FIELD

The present disclosure relates a wearable patch that has various functions of, e.g., obtaining biological information of a wearer by being attached directly to the human skin for medical purposes or the like. Moreover, the present disclosure relates to a sheet-type cell that is thin and can also be used as an operating power source of a wearable patch. In particular, the present disclosure relates to a wearable patch and a sheet-type cell that can easily be disposed of after use.

BACKGROUND ART

In recent years, patch-type devices that obtain biological information for medical purposes have come into widespread use. The patch-type devices can be attached directly to the surface of the skin and acquire biological information, including body temperature and heart rate.

Such a wearable device includes a sensor electrode, a drive circuit unit, and a cell, which are provided on the surface of a resin base. The sensor electrode is a functional element that is brought into contact with the skin to obtain biological information. The drive circuit unit receives the information from the sensor electrode and includes a transmitter that transmits the information to another device such as a smartphone. The cell serves as an operating power source of the drive circuit unit. Moreover, the wearable device can be attached to the skin as a patch when an adhesive layer is formed on the portion facing the skin other than the sensor electrode. Thus, the wearable device may be a wearable medical device that is used in direct contact with the body.

For example, Patent Document 1 discloses a body temperature measuring patch that includes a printed electrochemical cell with an anode and a cathode as a power source and an electric circuit including a flexible sensor. The electrochemical cell and the electric circuit are arranged between two resin substrate layers, each of which has an adhesive layer on the surface. The patch can perform data communication with a smartphone.

Patent Document 2 discloses a biometric patch that uses various sensors to measure the user's heart rate, respiration, activity, posture, etc. The biometric patch includes a reusable sensor device and a cell such as a zinc air cell. The sensor device includes, e.g., a sensor, a processor, an application, and a transmitter. The sensor device and the cell are contained in a disposable patch device including a plurality of layers such as a foam layer and an adhesive layer.

Patent Document 3 discloses a medical patch-type module that includes a resin substrate, electronic components including a sensor and a semiconductor device, and a coin-type air cell used as an operating power source of the electronic components. The electronic components and the air cell are mounted on the substrate. The module further includes a protection sheet that covers an adhesion layer for adhering the substrate to the human body. The protection sheet also serves as a sealing member that covers the side of the air cell where a positive electrode is provided. Therefore, when the protection sheet is peeled off and the module is attached to the human body, air comes into contact with the positive electrode, so that the air cell starts supplying power.

Moreover, many attempts have recently been made to use sheet-type cells as power sources of, e.g., various sensors of wearable devices such as a body temperature patch and head speed sensors for golf clubs. Under these circumstances, many improvements in various properties of the sheet-type cells have also been made, and sheet-type outer case members as well as internal members (a positive electrode, a negative electrode, a separator, an electrolyte, etc.) have been studied. For example, Patent Document 4 discloses a sheet-type cell (laminated cell) in which an adhesive portion is formed around a sheet-type outer case, and a priority peeling portion and a tension buffer portion are provided in part of the adhesive portion. The priority peeling portion peels earlier than the remaining part of the adhesive portion. The tension buffer portion is located adjacent to the priority peeling portion in the circumferential direction of the adhesive portion. The elongation rate of the tension buffer portion with respect to the tension acting in the circumferential direction of the adhesive portion is larger than that of the other part of the adhesive portion. With this configuration, the internal gas can be safely discharged from the priority peeling portion when the internal pressure is increased.

PRIOR ART DOCUMENTS

Patent Documents

Patent Document 1: JP 2016-505808 A
Patent Document 2: JP 2016-515022 A
Patent Document 3: JP 2017-370 A
Patent Document 4: JP 2006-351431 A

DISCLOSURE OF INVENTION

Problem to be Solved by the Invention

Such a medical patch is directly attached to the human body and therefore will be disposed of after each use for hygienic reasons. In some cases, the function of a wearable patch may be designed for one-time use. This wearable patch should be disposed of once its use is over.

If the used wearable patch is disposed of, while the cell capacity is left in the cell mounted on the wearable patch, the drive circuit unit will continue to operate even after disposal, which can cause unwanted chemical reactions or may result in unexpected situations such as heat generation and ignition. Moreover, in Europe and other countries, there are regulations that cells cannot be disposed of with other waste if the cells are still able to supply electricity. The problem is how to safely dispose of the wearable patch after use.

For example, Patent Document 2 teaches that the sheet member (patch device) and the sensor device (i.e., a circuit portion including the cell) can be separated from each other. The sheet member will be disposed of and the circuit portion will be reused. However, a new cell needs to be reinstalled for reuse, and it will take considerable time and cost to separate the circuit portion from the sheet member, and then to recover it for recycling in the actual use environment such as the medical field.

When the sheet-type cell used as a power source of the patch is a primary cell, the user may dispose of the cell after it has been fully discharged and dead. On the other hand, when the sheet-type cell is a secondary cell that can be used in a user-replaceable device, the user may remove the cell from the device for replacement after the cell capacity is low due to repeated charge and discharge, and then may dispose of the cell.

As described above, even if it is assumed that the user will dispose of the sheet-type cell, a current can flow by, e.g., the contact between the connection terminal of the sheet-type cell and a metal member. This may also result in unexpected situations, as in the case of the wearable patch. Therefore, it is desirable that the power supply can easily be interrupted and the sheet-type cell can be disposed of safely.

With the foregoing in mind, it is a first problem of the present disclosure to provide a wearable patch that can reliably interrupt the power supply from the cell after use and can be disposed of as it is. Moreover, it is a second problem of the present disclosure to provide a sheet-type cell that is used, e.g., as a power source of a wearable patch, and that can reliably interrupt the power supply after use and can be disposed of safely.

Means for Solving Problem

A wearable patch disclosed in the present application to solve the first problem is worn on the body and includes a functional element, a drive circuit unit that operates the functional element, and a cell as a power source. A cutting facilitating member is formed to allow a predetermined portion of the wearable patch to be cut with a force of 200 N or less so that power supply from the cell to the drive circuit unit is interrupted.

A sheet-type cell disclosed in the present application to solve the second problem includes power generation elements, including a sheet-type positive electrode and a sheet-type negative electrode, that are sealed in a sheet-type outer case. A cutting facilitating member is formed to allow a predetermined portion of the sheet-type cell to be cut with a force of 200 N or less so that power supply from the cell to the outside is interrupted.

Effects of the Invention

The wearable patch of the present application has the cutting facilitating member that allows a predetermined portion of the wearable patch to be cut with a force of 200 N or less and interrupts the power supply from the cell (power source) to the drive circuit unit. Thus, the wearable patch after use will not easily operate and can be disposed of safely.

The sheet-type cell of the present application has the cutting facilitating member that allows a predetermined portion of the sheet-type cell to be cut with a force of 200 N or less and interrupts the power supply from the cell (power source) to the outside. Thus, the sheet-type cell after use will not supply power to the outside and can be disposed of safely.

DESCRIPTION OF THE INVENTION

Figure 1:
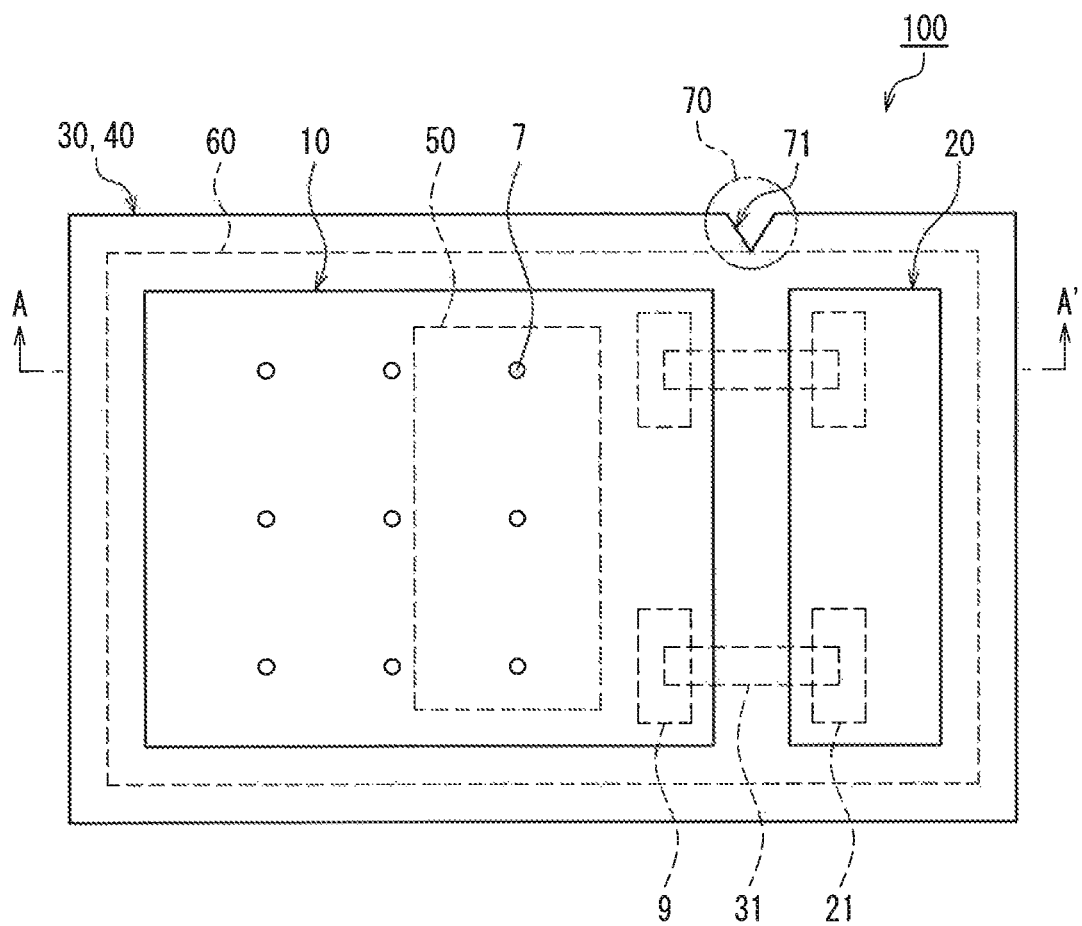
FIG. 1 is a plan view illustrating the schematic configuration of a wearable patch of Embodiment 1.

A wearable patch of the present disclosure is worn on the body and includes a functional element, a drive circuit unit that operates the functional element, and a cell as a power source. A cutting facilitating member is formed to allow a predetermined portion of the wearable patch to be cut with a force of 200 N or less so that the power supply from the cell to the drive circuit unit is interrupted.

With this configuration, the wearable patch of the present disclosure can be used as a medical measuring device or a drug administration device by operating the functional element. The wearable patch can also be used as a wearable device that acquires various physical information of the wearer. For disposal of the wearable patch, since the cutting facilitating member allows a predetermined portion of the wearable patch to be cut with a relatively small force of 200 N or less, it is possible to cut the wearable patch with both hands without using, e.g., scissors, and thus the power supply from the cell to the drive circuit unit can easily be interrupted. Therefore, during actual use of the wearable patch in the medical field or the home, the wearable patch after use can be disposed of safely.

The wearable patch may include a conductive path that connects the cell and the drive circuit unit. The conductive path can be cut by the cutting facilitating member. Since the cutting facilitating member allows the conductive path to be cut with a force of 200 N or less, the power supply from the cell to the drive circuit unit can be interrupted easily and reliably.

The cell may include power generation elements, including a positive electrode and a negative electrode, that are placed inside a sheet-type outer case, and a positive electrode terminal and a negative electrode terminal that are connected to the positive electrode and the negative electrode, respectively, to feed power generated by the power generation elements to the outside. At least one of the positive electrode terminal and the negative electrode terminal can be cut by the cutting facilitating member. Since the cutting facilitating member allows at least one of the terminals of the cell to be cut with a force of 200 N or less, the power supply from the cell can easily be interrupted.

The cell may be a sheet-type cell that includes power generation elements, including a sheet-type positive electrode and a sheet-type negative electrode, that are placed inside a sheet-type outer case. The power generation elements can be cut by the cutting facilitating member. When the sheet-type cell is used, it is also possible to cut the power generation elements themselves. Thus, the operation of the cell is stopped by cutting the power generation elements with a force of 200 N or less, and then the power supply from the cell can be interrupted.

The wearable patch may have a cutting start portion as the cutting facilitating member. The cutting start portion serves as a starting point for cutting. In this case, the cutting start portion may include a cut formed in the edge of the wearable patch.

The wearable patch may have a cut tape as the cutting facilitating member. The cut tape is provided so that the predetermined portion can be cut by pulling up one end of the cut tape that is located at the edge of the wearable patch.

The wearable patch may have a cutting portion as the cutting facilitating member. The cutting portion can easily be cut compared to other portions. In this case, the cutting portion may include perforations.

A sheet-type cell of the present disclosure includes power generation elements, including a sheet-type positive electrode and a sheet-type negative electrode, that are sealed in a sheet-type outer case. A cutting facilitating member is formed to allow a predetermined portion of the sheet-type cell to be cut with a force of 200 N or less so that the power supply from the cell to the outside is interrupted.

With this configuration, for disposal of the sheet-type cell of the present disclosure, since the cutting facilitating member allows a predetermined portion of the sheet-type cell to be cut with a relatively small force of 200 N or less, it is possible to cut the sheet-type cell with both hands without using, e.g., scissors, and thus the power supply from the cell to the outside can easily be interrupted. Therefore, during actual use of the sheet-type cell in the medical field or the home, the sheet-type cell after use can be disposed of safely.

The sheet-type cell may include a positive electrode terminal and a negative electrode terminal that are connected to the positive electrode and the negative electrode, respectively, to feed power generated by the power generation elements to the outside. At least one of the positive electrode terminal and the negative electrode terminal can be cut by the cutting facilitating member. Since the cutting facilitating member allows the positive electrode terminal and/or the negative electrode terminal to be cut with a force of 200 N or less, the power supply from the cell to the outside can be interrupted easily and reliably.

In the sheet-type cell, the power generation elements can be cut by the cutting facilitating member. Thus, the operation of the cell is stopped by cutting the power generation elements with a force of 200 N or less, and then the power supply from the cell can be interrupted.

The sheet-type cell may have a cutting start portion as the cutting facilitating member. The cutting start portion serves as a starting point for cutting. In this case, the cutting start portion may include a cut formed in the edge of the sheet-type cell.

The sheet-type cell may have a cut tape as the cutting facilitating member. The cut tape is provided so that the predetermined portion can be cut by pulling up one end of the cut tape that is located at the edge of the sheet-type cell.

The sheet-type cell may have a cutting portion as the cutting facilitating member. The cutting portion can easily be cut compared to other portions. In this case, the cutting portion may include perforations.

Hereinafter, the wearable patch and the sheet-type cell of the present disclosure will be described with reference to the drawings.

The drawings that illustrate the structures of the wearable patch and the sheet-type cell of this embodiment are intended to clarify the shapes of the members constituting the wearable patch or the sheet-type cell and the correlation between their positions. Thus, the size of each member in the drawings does not necessarily reflect the actual size.

The following description is illustrative only, and the configurations of the wearable patch and the sheet-type cell disclosed in the present application are not limited to embodiments as will be described below.

<Embodiments of Wearable Patch Disclosed in the Present Application>

First, embodiments of a wearable patch disclosed in the present application will be described.

Embodiment 1

A wearable patch of the present application has a cutting facilitating member that allows the wearable patch to be cut with a force of 200 N or less. In Embodiment 1, the wearable patch includes a cutting start portion as the cutting facilitating member.

The cutting start portion is formed in the edge of the wearable patch, and the force required to start cutting the wearable patch can be smaller in this portion than in the other portions. Therefore, when the cutting of the wearable patch starts from the cutting start portion, the wearable patch can be cut substantially linearly using the cutting start portion as a starting point with a relatively small force of 200 N or less. The force that would be required to start cutting the wearable patch usually reaches the maximum value if the wearable patch is cut with both hands without using tools such as scissors. However, this value can be reduced by forming the cutting start portion, so that the wearable patch can be cut with a relatively small force.

[Configuration of Wearable Patch]

Figure 2:
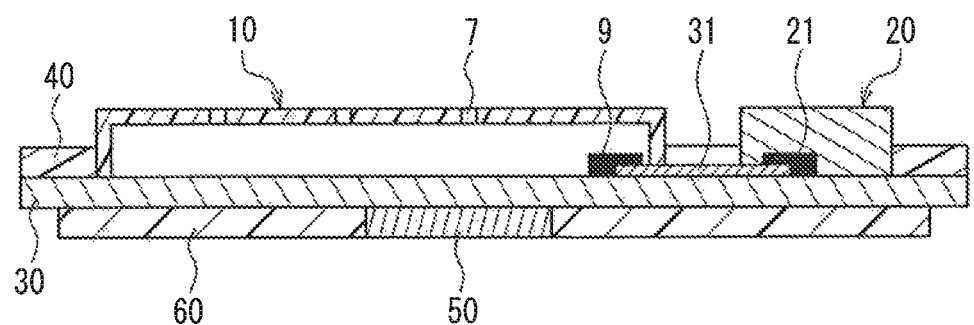
FIG. 2 is a cross-sectional view illustrating the schematic configuration of a wearable patch of Embodiment 1.

FIG. 1 is a plan view illustrating the schematic configuration of the wearable patch of this embodiment. FIG. 2 is a cross-sectional view illustrating the schematic configuration of the wearable patch of this embodiment.

FIG. 2 shows the cross section taken along the line A-A' in FIG. 1. FIGS. 1 and 2 are intended to explain the schematic configuration of the entire wearable patch 100, and the members constituting the wearable patch 100 are simplified. In the following description, for the sake of convenience, the vertical direction in FIG. 2 is defined as the vertical direction of the wearable patch 100 of this embodiment. Specifically, when the wearable patch 100 is attached to the body, the side facing the skin of the wearer is the lower surface of the wearable patch 100 and the side facing the outside is the upper surface of the wearable patch 100.

The wearable patch 100 of this embodiment may be, e.g., a medical patch for detecting the body temperature of the wearer and is used in direct contact with the skin.

As shown in FIG. 1, the wearable patch 100 of this embodiment includes a cell 10 as an operating power source and a drive circuit unit 20 for operating the wearable patch 100. The cell 10 and the drive circuit unit 20 are placed on the upper surface of a base 30. Moreover, electrode terminals 9 are formed on the underside of the cell 10 and connection terminals 21 are formed on the underside of the drive circuit unit 20. Further, power supply wires 31 (conductive path) are formed on the upper surface of the base 30 that serves as a substrate of the entire wearable patch 100. The electrode terminals 9 and the connection terminals 21 are connected by the power supply wires 31 to supply power from the cell 10 to the drive circuit unit 20.

The upper surface of the base 30 is covered with a cover member 40 other than the region where the cell 10 and the drive circuit unit 20 are placed.

A functional element 50 and an adhesive layer 60 are formed on the lower surface of the base 30. The functional element 50 is brought into contact with or in close proximity to the skin of the wearer. The adhesive layer 60 is used to attach the wearable patch 100 to the person to be measured. The drive circuit unit 20 and the functional element 50 are connected by, e.g., a connection wire (not shown). The functional element 50 has predetermined functions of, e.g., detecting biological information such as body temperature and heart rate and injecting a drug solution in accordance with the control of the drive circuit unit 20.

The wearable patch 100 of this embodiment has a cut 71 as a cutting start portion 70 that allows the wearable patch 100 to be cut with a force of 200 N or less. The cut 71 is formed in the edge of the wearable patch, where the base 30 and the cover member 40 are laminated. To dispose of the wearable patch 100, the wearable patch 100 is cut from the cut 71 of the cutting start portion 70 as a starting point. This can disconnect the conductive path (i.e., the power supply wires 31) for supplying power from the cell 10 to the drive circuit unit 20, which is a predetermined portion of the wearable patch 100. Thus, the power supply can be reliably interrupted.

Hereinafter, configuration examples of the members of the wearable patch 100 of this embodiment will be described.

[Cell]

The cell 10 is used as an operating power source and mounted on the wearable patch 100 that is to be attached to the surface of the skin. The cell 10 is not particularly limited and may be, e.g., a cell that includes an electrolyte solution containing water as a solvent (dry cell such as alkaline cell or manganese cell, air cell, etc.) or a cell that includes a nonaqueous electrolyte solution containing a nonaqueous solvent (lithium cell etc.). It is preferable that the cell is thin and lightweight to avoid making the wearer feel uncomfortable, and that the cell has a large cell capacity to allow the drive circuit unit 20 to operate for a long time. In view of this, the wearable patch 100 uses the sheet-type air cell 10 as an operating power source because the power generation elements, including the positive electrode and the negative electrode, and the outer case members of the cell are in the form of sheets.

Figure 3:
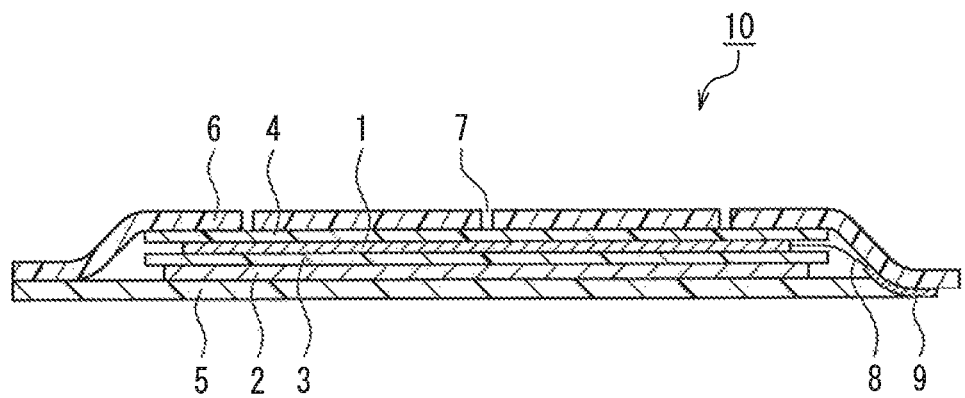
FIG. 3 is a cross-sectional view illustrating the configuration of an air cell as a power source.

FIG. 3 is a cross-sectional view illustrating the configuration of the sheet-type air cell 10 used in the wearable patch 100 of this embodiment.

Figure 4:
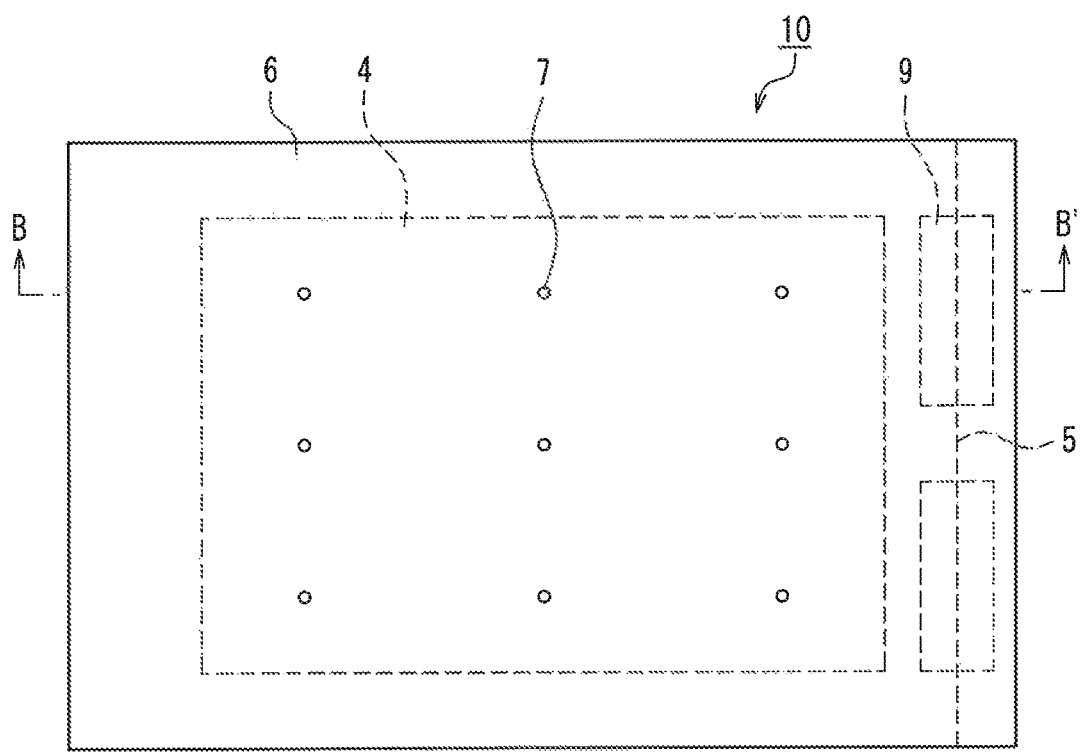
FIG. 4 is a plan view illustrating the configuration of an air cell as a power source.

FIG. 4 is a plan view illustrating the configuration of the sheet-type air cell 10 used in the wearable patch 100 of this embodiment. FIG. 3 shows the cross section taken along the line B-B' in FIG. 4.

In the sheet-type air cell 10, each of the members such as the power generation elements, including the positive electrode and the negative electrode, is formed into a sheet. Accordingly, the sheet-type air cell 10 has a sheet shape with flexibility as a whole.

As shown in FIG. 3, the sheet-type air cell 10 includes a sheet-type positive electrode 1, a sheet-type negative electrode 2, a separator 3 provided between the positive electrode 1 and the negative electrode 2, an electrolyte solution (not shown), a sheet-type outer case member 6 located on the positive electrode 1 side, and a sheet-type outer case member 5 located on the negative electrode 2 side. The edges of the outer case members 5, 6 are sealed so that the positive electrode 1, the negative electrode 2, the separator 3, and the electrolyte solution are hermetically sealed between the outer case members 5, 6. Moreover, a water repellent membrane 4 is placed between the positive electrode 1 and the outer case member 6. The water repellent membrane 4 is permeable to air, but impermeable to water (electrolyte solution). Air holes 7 are formed in the outer case member 6, and air (oxygen) is supplied from the air holes 7 via the water repellent membrane 4 to the positive electrode 1 and functions as a positive electrode active material.

As shown in FIGS. 1 and 2, in the wearable patch 100 of this embodiment, since the air cell 10 is placed on the upper surface of the base 30, the cover member 40 has an opening so as to expose the surface of the air cell 10 and not to cover the air holes 7 provided in the outer case member 6 of the air cell 10.

Hereinafter, the members of the sheet-type air cell 10 will be described in detail.

(Positive Electrode)

The positive electrode 1 has a catalyst layer. For example, the positive electrode with a laminated structure of the catalyst layer and a current collector may be used.

The catalyst layer may contain, e.g., a catalyst and a binder.

Examples of the catalyst of the catalyst layer include the following: silver; platinum metals or alloys thereof, transition metals; platinum/metal oxides such as $Pt/IrO_2$; perovskite oxides such as $La_{1-x}Ca_xCoO_3$; carbides such as WC; nitrides such as $Mn_4N$; manganese oxides such as manganese dioxide; and carbon (including, e.g., graphite, carbon black (acetylene black, Ketjenblack, channel black, furnace black, lamp black, thermal black, etc.), charcoal, and activated carbon). These catalysts may be used alone or in combinations of two or more.

The heavy metal content in the catalyst layer, except for the components of the electrolyte solution, is preferably 1% by mass or less. When the positive electrode has the catalyst layer with a low heavy metal content, the environmental impact can be reduced even if the cell is disposed of without any special treatment. In this regard, the above carbon is more preferred as the catalyst. The heavy metal content in the catalyst layer can be measured by X-ray fluorescence analysis. For example, the measurement can be performed using an X-ray fluorescence analyzer "ZSX100e (product name)" manufactured by Rigaku Corporation under the following conditions: excitation source, Rh 50 kV; and analysis area, φ 10 mm.

In terms of further improving the reactivity of the positive electrode, the specific surface area of the carbon that is used as the catalyst is preferably 200 $m^2/g$ or more, more preferably 300 $m^2/g$ or more, and further preferably 500 $m^2/g$ or more. The specific surface area of the carbon is determined by a BET method in accordance with JIS K 6217. For example, the specific surface area of the carbon can be measured with a specific surface area measuring device based on a nitrogen adsorption method. The upper limit of the specific surface area of the carbon is usually about 2000 $m^2/g$.

The content of the catalyst in the catalyst layer is preferably 20 to 70% by mass.

Examples of the binder of the catalyst layer include fluorocarbon resin binders such as PVDF, PTFE, copolymers of vinylidene fluoride, and copolymers of tetrafluoroethylene (including, e.g., a vinylidene fluoride-hexafluoropropylene copolymer (PVDF-HFP), a vinylidene fluoride-chlorotrifluoroethylene copolymer (PVDF-CTFE), a vinylidene fluoride-tetrafluoroethylene copolymer (PVDF- TFE), and a vinylidene fluoride-hexafluoropropylene-tetrafluoroethylene copolymer (PVDF-HFP-TFE)). Among them, polymers of tetrafluoroethylene (PTFE) or copolymers of tetrafluoroethylene are preferred, and PTFE is more preferred. The content of the binder in the catalyst layer is preferably 3 to 50% by mass.

The positive electrode having the catalyst layer can be produced by, e.g., mixing the above catalyst, binder, or the like with water, rolling the mixture between rotating rolls, and bringing the rolled material into close contact with a current collector. There may be another way of producing the positive electrode. First, a composition (slurry, paste, etc.) for forming a catalyst layer is prepared by dispersing the above catalyst and optionally the binder or the like in water or an organic solvent. Then, the composition is applied to the surface of a current collector and dried, which is further subjected to pressing (e.g., calendering) as needed.

The current collector of the positive electrode having the catalyst layer or a positive electrode mixture layer may be, e.g., a mesh, foil, expanded metal, or punched metal made of metals such as titanium, nickel, stainless steel, and copper or may be, e.g., a mesh or porous sheet made of carbon. The thickness of the current collector of the positive electrode is preferably 10 to 300 μm.

Moreover, when the sheet-type outer case member is formed of a resin film or a laminated material of a resin film and a metal film, the resin film or a part of the laminated material may also be used as the current collector of the positive electrode. In such a case, e.g., the current collector can be provided by applying a carbon paste to the surface of the resin film or the laminated material that is to be the inner surface of the sheet-type outer case member. Alternatively, the metal layer of the laminated material can also serve as the current collector. Then, the positive electrode mixture layer or the catalyst layer can be formed on the surface of the current collector in the same manner as described above, thus producing the positive electrode. The thickness of the carbon paste layer is preferably 30 to 300 μm.

(Negative Electrode)

The negative electrode 2 may be formed of, e.g., metal particles or metal foil containing a metal material. Examples of the metal material include the following: a zinc-based material (which collectively refers to both a zinc material and a zinc alloy material); a magnesium-based material (which collectively refers to both a magnesium material and a magnesium alloy material); and an aluminum-based material (which collectively refers to both an aluminum material and an aluminum alloy material). In this negative electrode, metals such as zinc, magnesium, and aluminum act as an active material.

The alloy constituents of the zinc alloy material may be, e.g., indium (the content is, e.g., 0.005 to 0.05% by mass), bismuth (the content is, e.g., 0.005 to 0.05% by mass), and aluminum (the content is, e.g., 0.001 to 0.15% by mass).

The alloy constituents of the magnesium alloy material may be, e.g., calcium (the content is, e.g., 1 to 3% by mass), manganese (the content is, e.g., 0.1 to 0.5% by mass), zinc (the content is, e.g., 0.4 to 1% by mass), and aluminum (the content is, e.g., 8 to 10% by mass).

The alloy constituents of the aluminum alloy material may be, e.g., zinc (the content is, e.g., 0.5 to 10% by mass), tin (the content is, e.g., 0.04 to 1.0% by mass), gallium (the content is, e.g., 0.003 to 1.0% by mass), silicon (the content is, e.g., 0.05% by mass or less), iron (the content is, e.g., 0.1% by mass or less), magnesium (the content is, e.g., 0.1 to 2.05% by mass), and manganese (the content is, e.g., 0.01 to 0.5% by mass).

The negative electrode may contain only one type of metal particles or two or more types of metal particles.

In view of a reduction in the environmental impact of the cell for disposal, it is preferable that the metal material used for the negative electrode contains the smallest possible amount of mercury, cadmium, lead, and chromium. Specifically, it is more preferable that the mercury content is 0.1% by mass or less, the cadmium content is 0.01% by mass or less, the lead content is 0.1% by mass or less, and the chromium content is 0.1% by mass or less.

The particle size of the zinc-based material may be defined as follows. For example, the proportion of the particles with a particle diameter of 75 μm or less is preferably 50% by mass or less, and more preferably 30% by mass or less of all particles. Moreover, the proportion of the particles with a particle diameter of 100 to 200 μm may be 50% by mass or more, and more preferably 90% by mass or more of all particles.

The particle size of the magnesium-based material and the aluminum-based material may be defined as follows. For example, the proportion of the particles with a particle diameter of 30 μm or less is preferably 50% by mass or less, and more preferably 30% by mass or less of all particles. Moreover, the proportion of the particles with a particle diameter of 50 to 200 μm may be 50% by mass or more, and more preferably 90% by mass or more of all particles.

In the above description, the particle size of the metal particles means a particle diameter ($D_{50}$) at a cumulative frequency of 50% in the volume-based distribution, which is measured with a laser scattering particle size distribution analyzer by dispersing the particles in a medium that does not dissolve those particles.

When the negative electrode contains the metal particles, e.g., a gelling agent (such as sodium polyacrylate or carboxymethyl cellulose) and a binder may be added as needed. This may be mixed with an electrolyte solution to form a negative electrode agent (such as a gel-like negative electrode). The amount of the gelling agent in the negative electrode is preferably, e.g., 0.5 to 1.5% by mass. The amount of the binder in the negative electrode is preferably 0.5 to 3% by mass.

The electrolyte solution used for the negative electrode containing the metal particles may be the same as that injected into the cell.

The content of the metal particles in the negative electrode is preferably, e.g., 60% by mass or more, and more preferably 65% by mass or more. The content of the metal particles in the negative electrode is also preferably 95% by mass or less, and more preferably 90% by mass or less.

The negative electrode containing the metal particles preferably contains an indium compound such as indium oxide or indium hydroxide. The presence of the indium compound in the negative electrode can more effectively prevent the generation of hydrogen gas due to a corrosion reaction between the metal particles and the electrolyte solution.

The amount of the indium compound in the negative electrode is preferably 0.03 to 1 with respect to 100 of the metal particles at a mass ratio.

The negative electrode may also be a metal sheet (such as metal foil) made of, e.g., the zinc-based material or the magnesium-based material. Such a negative electrode preferably has a thickness of 10 to 500 μm.

The negative electrode may include a current collector as needed in order to improve the current collection properties. The current collector of the negative electrode may be, e.g., a mesh, foil, expanded metal, or punched metal made of metals such as nickel, copper, and stainless steel or may be, e.g., a sheet or mesh made of carbon. The thickness of the current collector of the negative electrode is preferably 10 to 300 µm.

Like the positive electrode, the current collector of the negative electrode can be provided by applying a carbon paste to the surface that is to be the inner surface of the sheet-type outer case member. Alternatively, the metal layer of the outer case member can also serve as the current collector. The thickness of the carbon paste layer is preferably 50 to 200 µm.

(Separator)

The separator 3 may be any separator that is generally used in various cells. Examples of the separator include a porous resin film (such as a microporous film or nonwoven fabric) and a semipermeable membrane typified by a cellophane film. In terms of preventing a short circuit of the sheet-type cell and improving the load characteristics, the separator is preferably made of a semipermeable membrane.

When the separator is made of a resin porous film, polyolefins such as polyethylene (PE), polypropylene (PP), and an ethylene-propylene copolymer may be used.

The resin separator preferably has a porosity of 30 to 80% and a thickness of 10 to 100 µm.

When the separator is made of a semipermeable membrane such as a cellophane film, it may consist only of the semipermeable membrane. However, the semipermeable membrane can easily be damaged during cell assembly because of its low strength. Therefore, it is also recommended that the separator should be made of a laminated material of the semipermeable membrane and a grafted film of a particular polymer.

The graft polymer constituting the grafted film is composed of, e.g., (meth)acrylic acid or its derivative that is graft-polymerized onto polyolefin (polyethylene, polypropylene, etc.), which is a backbone polymer. However, any graft polymer in this form can be used and is not limited to the method of graft polymerization of (meth)acrylic acid or its derivative onto polyolefin.

When the separator consists only of a cellophane film, the thickness of the separator is preferably, e.g., 15 µm or more. The thickness of the separator is also preferably 40 µm or less, and more preferably 30 µm or less.

When the separator is made of a laminated material of a grafted film and a cellophane film, the thickness of the separator, i.e., the total thickness of the grafted film and the cellophane film is preferably, e.g., 30 µm or more, and more preferably 40 µm or more. The thickness of the separator is also preferably 70 µm or less, and more preferably 60 µm or less.

Moreover, when the separator is made of a laminated material of a grafted film and a cellophane film, the thickness of the grafted film is preferably, e.g., 15 µm or more, and more preferably 25 µm or more. The thickness of the grafted film is also preferably 30 µm or less.

The laminated material of the grafted film and the cellophane film used for the separator is commercially available, e.g., from Yuasa Membrane Systems Co., Ltd. under the name of "YG9132", "YG9122", or "YG2152".

The separator may be formed by combining, e.g., the cellophane film or both the cellophane film and the grafted film with a liquid-absorbing layer (i.e., an electrolyte solution holding layer) such as vinylon-rayon mixed paper. In this case, the thickness of the liquid-absorbing layer is preferably 20 to 500 µm.

(Outer Case Member) The sheet-type outer case members 5, 6 may be formed of a resin film.

Examples of the resin film include a nylon film (such as a nylon 66 film) and a polyester film (such as a polyethylene terephthalate (PET) film). The thickness of the resin film is preferably 20 to 100 m.

The sheet-type outer case members 5, 6 are generally sealed by heat-sealing the edge of the outer case member 6 located on the positive electrode 1 side and the edge of the outer case member 5 located on the negative electrode 2 side. To further facilitate the heat seal, each of the outer case members 5, 6 may include a heat-sealing resin layer that is formed on the resin film. The heat-sealing resin of the heat-sealing resin layer may be, e.g., a modified polyolefin film (such as a modified polyolefin ionomer film) or polypropylene and its copolymer. The thickness of the heat-sealing resin layer is preferably 20 to 100 µm.

Moreover, a metal layer may be formed on the resin film. The metal layer may be, e.g., an aluminum film (including aluminum foil and aluminum alloy foil) or a stainless steel film (including stainless steel foil). The thickness of the metal layer is preferably 10 to 150 µm.

The resin film of the sheet-type outer case members 5, 6 may be, e.g., a laminated film of the heat-sealing resin layer and the metal layer.

Each of the sheet-type outer case members is quadrangular in a plan view as a suitable shape for the air cell. However, the shape of the sheet-type outer case members 5, 6 of the air cell 10 is not limited to a quadrangle in a plan view and may be, e.g., a polygon (such as triangle, pentagon, hexagon, heptagon, or octagon), a circle, or an ellipse in accordance with the shape of the equipment used or the shape of a portion where the air cell is to be placed.

As shown in FIGS. 3 and 4, the air cell 10 of this embodiment has the air holes 7. The air holes 7 are formed in the outer case member 6 and provided at the position overlapping the positive electrode 1.

The outside air is taken through the air holes 7 and oxygen in the air functions as a positive electrode active material to supply electricity. Each of the air holes 7 may be, e.g., a circular opening with a diameter of about 50 µm to 1 mm. The air holes 7 may be formed in the outer case member 6 by, e.g., a laser irradiation method or a mechanical punching method.

In FIG. 4, a total of nine air holes 7 are arranged in a matrix of 3 rows and 3 columns. The number and arrangement of the air holes 7 are not particularly limited. It is preferable that the air holes 7 are dispersed as evenly as possible in a plan view so that the amount of oxygen required for the positive electrode 1 can be supplied. Moreover, the shape of the air holes 7 is not limited to substantially circular as illustrated in FIG. 4 and may be, e.g., rectangular or elliptical.

In the air cell 10 of this embodiment, a portion near one side of the outer case member 6 is not thermally fused to the outer case member 5 and both surfaces of this portion are exposed. Two electrode terminals 9 are formed on one of the exposed surfaces of the outer case member 6 that faces the negative electrode 2.

The electrode terminals 9 may be made of a conductor such as a metal thin film or a carbon paste obtained by, e.g., vapor deposition or printing. In FIG. 4, one of the electrode terminals 9 that is located on the upper side is connected to the positive electrode 1 with a lead wire 8 or the like. The other electrode terminal 9 is electrically connected to the negative electrode 2 (not shown). As shown in FIGS. 3 and 4, the outer case members 5, 6 are sealed with the edge of the outer case member 5 being positioned substantially in the middle of the electrode terminals 9. In this manner, the electrode terminals 9 can be exposed to the lower surface of the air cell 10, and thus power is supplied to the drive circuit unit 20 via the power supply wires 31 (see FIGS. 1 and 2) provided on the upper surface of the base 30.

In addition to the above method, there may be another way of exposing the electrode terminals 9 to the lower surface of the air cell 10. An opening is formed in advance in the outer case member 5 at the location where the outer case member 6 is to be thermally fused to the outer case member 5. The outer case members 5, 6 are sealed so that the electrode terminals 9 are placed between the opening and the outer case member 6.

The electrode terminals of the air cell 10 are formed on the inner surface of the outer case member 6, as shown in FIGS. 3 and 4. Moreover, the electrode terminals may have a via structure penetrating the outer case member 5. With this configuration, the electrode terminals can be brought into contact with the power supply wires 31 provided under the air cell 10.

(Water Repellent Membrane)

In the sheet-type air cell 10, the water repellent membrane 4 is placed between the positive electrode 1 and the outer case member 6. The water repellent membrane has not only water repellency, but also air permeability. Specifically, such a water repellent membrane may be composed of, e.g., fluororesin such as PTFE or resin such as polyolefin (polypropylene, polyethylene, etc.). The thickness of the water repellent membrane may be 50 to 250 μm.

Moreover, an air diffusion membrane may be provided between the outer case member 6 and the water repellent membrane 4. The air diffusion membrane serves to supply the air that has been taken inside the outer case member 6 to the positive electrode. The air diffusion membrane may be, e.g., a nonwoven fabric made of resin such as cellulose, polyvinyl alcohol, polypropylene, or nylon. The thickness of the air diffusion membrane may be 100 to 250 μm.

(Electrolyte Solution) The electrolyte salt of the electrolyte solution contained between the two sheet-type outer case members 5, 6 is not particularly limited. Examples of the electrolyte salt include the following: salts of alkali metals such as sodium chloride; and salts of strong acids and weak bases. The strong acids may be selected from, e.g., hydrochloric acid, sulfuric acid, and nitric acid. The weak bases may be typified by ammonia and hydroxides of metallic elements such as aluminum hydroxide and magnesium hydroxide. Among them, the salts of strong acids and weak bases are preferred, and ammonium salts or salts of particular metallic elements are more preferred.

Specifically, salts of at least one type of ions selected from $Cl^-$, $SO_4^{2-}$, $HSO_4^-$, and $NO_3^-$ and at least one type of ions selected from Al ions, Mg ions, Fe ions, and ammonium ions may be used. Examples of the salts include the following: ammonium salts such as ammonium sulfate, ammonium hydrogen sulfate (($NH_4$)$HSO_4$), ammonium chloride, and ammonium nitrate; aluminum salts such as aluminum sulfate, aluminum chloride, and aluminum nitrate; magnesium salts such as magnesium sulfate, magnesium chloride, magnesium chloride hydroxide (MgCl(OH)), and magnesium nitrate; and iron salts such as iron (II) sulfate, iron (II) ammonium sulfate (($NH_4$)$_2$Fe($SO_4$)$_2$), iron (III) sulfate, iron (II) chloride, and iron (II) nitrate.

Aqueous solutions containing the salts of strong acids and weak bases have a relatively weak corrosive action on a metal material that can be a negative electrode active material, and also have a relatively high conductivity. Thus, good discharge characteristics can be achieved.

The pH of the electrolyte solution is 3 or more and less than 12. This may result in an air cell with improved safety, a reduced environmental impact, and good discharge characteristics. The pH of the electrolyte solution is 3 or more, and preferably 5 or more. Furthermore, the pH of the electrolyte solution is less than 12, preferably 10 or less, and more preferably less than 7. The use of the above electrolyte salts can facilitate the adjustment of the pH of the electrolyte solution within the above range and can also make the electrolyte solution less irritating to the skin. Therefore, even if the electrolyte solution leaks due to damage to the outer case of the air cell and adheres to, e.g., the skin of the wearer of the wearable patch 100, it is less likely to cause trouble. Thus, the air cell is suitable as a power source for the wearable patch 100 that is directly attached to the body.

The electrolyte solution may be an aqueous solution that contains, as an electrolyte, only one of the salts of at least one type of ions selected from $Cl^-$, $SO_4^{2-}$, $HSO_4^-$, and $NO_3^-$ and at least one type of ions selected from Al ions, Mg ions, Fe ions, and ammonium ions. The aqueous solution may also contain two or more of the salts.

The salt of $Cl^-$ ions and $Fe^{3+}$ ions (i.e., iron (III) chloride) has a strong corrosive action on a metal material that can be a negative electrode active material, as compared to salts of other combinations of ions. Therefore, salts other than iron (III) chloride are preferably used. Moreover, ammonium salts are more preferred because they have a lower corrosive action on the metal material.

Although one of the salts of strong acids and weak bases, perchlorate may create a risk of combustion or explosion when it is heated or subjected to shock.

Therefore, from the viewpoint of environmental impact and safety of disposal, perchlorate should not be contained in the aqueous solution (i.e., the electrolyte solution). Even if it is contained, the amount of perchloric acid ions is preferably as small as possible (specifically less than 100 ppm, and more preferably less than 10 ppm). [0114]1 Among the above salts of strong acids and weak bases, heavy metal salts (other than iron salts) typified by, e.g., zinc chloride and copper sulfate are often harmful. Therefore, from the viewpoint of environmental impact and safety of disposal, heavy metal salts should not be contained in the aqueous solution (i.e., the electrolyte solution). Even if they are contained, the amount of heavy metal ions other than iron ions is preferably as small as possible (specifically less than 100 ppm, and more preferably less than 10 ppm).

The conductivity of the electrolyte solution is preferably 80 mS/cm or more. Accordingly, the concentration of the electrolyte in the aqueous solution (i.e., the electrolyte solution) may be determined to ensure such a conductivity. In this case, when the aqueous solution contains only one type of electrolyte, the above concentration means the concentration of that electrolyte. When the aqueous solution contains two or more types of electrolytes, the above concentration means the total concentration of those electrolytes. The concentration of the electrolyte is usually 5 to 50% by mass. The upper limit of the conductivity of the electrolyte solution is usually about 700 mS/cm.

It is preferable that an indium compound is dissolved in the electrolyte solution. When the indium compound is dissolved in the electrolyte solution, the generation of hydrogen gas inside the cell can be adequately suppressed.

Examples of the indium compound dissolved in the electrolyte solution include indium hydroxide, indium oxide, indium sulfate, indium sulfide, indium nitrate, indium bromide, and indium chloride.

The concentration of the indium compound in the electrolyte solution is preferably 0.005% by mass or more, more preferably 0.01% by mass or more, and particularly preferably 0.05% by mass or more. The concentration of the indium compound in the electrolyte solution is also preferably 1% by mass or less, more preferably 0.5% by mass or less, and particularly preferably 0.1% by mass or less.

In addition to the above components, the electrolyte solution may contain various known additives as needed. For example, zinc oxide may be added to the electrolyte solution to prevent corrosion (oxidation) of the metal material used for the negative electrode. In this case, zinc oxide also may be added to the negative electrode.

(Specifications of Air Cell) The overall shape of the sheet-type air cell 10, including the above members, may be, e.g., 30 to 50 mm on the long side and 20 to 35 mm on the short side. The air cell 10 preferably has a smaller thickness in order to facilitate the mounting of the cell on the wearable patch 100 and also to make the wearable patch 100 easily deformable when it is attached to the body. The thickness of the air cell 10 may be, e.g., 1 mm or less. In view of the stiffness of the air cell 10 required for handling and the cell capacity, the minimum value of the thickness may be, e.g., 0.2 mm.

Next, four sheet-type air cells were actually produced as examples by using four types of electrolyte solutions to examine the discharge capacity.

In each of the sheet-type air cells, the positive electrode, the negative electrode, the electrolyte solution, the separator, the water repellent membrane, and the outer case members were made of the following materials.

<Positive Electrode>

A composition for forming a catalyst layer was prepared by mixing 30 parts by mass of carbon (Ketjenblack EC600JD (trade name) manufactured by Lion Specialty Chemicals Co., Ltd.) with a DBP oil absorption of 495 cm$^3$/100 g and a specific surface area of 1270 m$^2$/g, 15 parts by mass of an acrylic dispersing agent, 60 parts by mass of SBR, and 500 parts by mass of water.

Using a porous carbon sheet (thickness: 0.25 mm, porosity: 75%, air permeability (Gurley): 70 sec/100 ml), the composition for forming a catalyst layer was applied to the surface of the base by stripe coating so that the coating amount after drying was 10 mg/cm$^2$. Then, the composition was dried, resulting in a current collector that had a portion in which the catalyst layer was formed and a portion in which no catalyst layer was formed. This current collector was punched into a shape including the portion with the catalyst layer that was 15 mm×15 mm in size and the portion without the catalyst layer that was 5 mm×15 mm in size. The portion without the catalyst layer was located at one end of the 15 mm×15 mm portion and was to be a lead. Thus, a positive electrode (air electrode) with a total thickness of 0.27 mm was produced.

<Negative Electrode>

Zinc alloy foil (thickness: 0.05 mm) containing additional elements of In: 0.05%, Bi: 0.04%, and Al: 0.001% was prepared. Then, the zinc alloy foil was punched into a shape including a portion that was 15 mm×15 mm in size and served as an active material, and a portion that was 5 mm×15 mm in size, was located at one end of the 15 mm×15 mm portion, and was to be a lead. Thus, a negative electrode was produced.

<Electrolyte solution>

Cell 1: 20% by mass of ammonium sulfate aqueous solution (pH=5.3) Cell 2: 20% by mass of ammonium chloride aqueous solution (pH=4.3) Cell 3: 20% by mass of sodium chloride aqueous solution (pH=7) Cell 4: 30% by mass of potassium hydroxide aqueous solution (pH=14)

<Separator>

A separator was produced by forming two graft films (each having a thickness of 15 μm) on both sides of a cellophane film (having a thickness of 20 μm). The graft films were composed of a graft copolymer obtained by graft copolymerization of acrylic acid with a polyethylene main chain.

<Water Repellent Membrane>

A water repellent membrane was a PTFE sheet with a thickness of 200 μm.

<Outer Case Member>

Two 2.5 cm×2.5 cm aluminum laminated films were used as outer case members. Each of the aluminum laminated films had a structure in which a PET film was provided on the outer surface of aluminum foil, and a polypropylene film (heat-sealing resin layer) was provided on the inner surface of the aluminum foil.

<Cell Assembly>

Nine air holes, each having a diameter of 0.5 mm, were formed in one of the two laminated films (outer case members), which was to be located on the positive electrode side. The air holes corresponded to the position of the catalyst layer of the positive electrode. The air holes were arranged in a matrix and spaced at regular intervals of 4.5 mm (length)×4.5 mm (width) (i.e., the center-to-center distance of adjacent air holes: 5 mm). Then, the water repellent membrane was thermally fused to the inner surface of this laminated film with a hot-melt adhesive. In the other laminated film, which was to be located on the negative electrode side, a modified polyolefin ionomer film was attached in parallel with the side of the laminated film to a portion where the leads of the positive electrode and the negative electrode were to be arranged, in order to improve the sealing properties of the thermally fused portion between the leads and the outer case member.

The laminated film having the water repellent membrane was put down, and then the positive electrode, the separator, and the negative electrode were formed in this order on the water repellent membrane. Moreover, the other laminated film was placed on top of them so that the modified polyolefin ionomer film was positioned on the leads of the positive electrode and the negative electrode. Next, three sides of the two laminated films were thermally fused to each other, thus providing a bag-like outer case. After the electrolyte solution was injected through the opening of the bag-like outer case, the opening was sealed by thermal fusion, and consequently a sheet-type air cell was obtained. The thickness of the air cell was approximately 1 mm.

Each of the air cells thus obtained was allowed to stand in the atmosphere for 10 minutes, and then discharged to 0.5 V at a current corresponding to the 100 hour rate with respect to the design capacity of the cell. At this time, the discharge capacity of the cell was measured. Table 1 shows the results.

TABLE 1

|  | Discharge capacity (mAh) |
| --- | --- |
| Cell 1 | 35 |
| Cell 2 | 33 |
| Cell 3 | 30 |
| Cell 4 | 36 |

Compared to the air cell (cell 4) including a high concentration alkaline electrolyte solution, which is used as an electrolyte solution of a commercially available coin-type air cell, the air cells (cells 1 to 3) including an electrolyte solution that is much safer than the alkaline electrolyte solution can achieve sufficient discharge capacity. In particular, the cells 1 and 2, in which the salts of strong acids and weak bases are used as electrolyte salts, can have excellent properties that are substantially the same as those of the cell 4 including the electrolyte solution similar to that of a commercially available button-type air cell.

The above results confirm that the air cell of this embodiment has a small thickness, good handleability, and high safety. Moreover, the air cell has a relatively large capacity and is suitable as a power source for a device that is directly attached to the body. Further, the air cell used as a power source is made of environmentally friendly materials. This is particularly preferred for the wearable patch 100 of this embodiment because the wearable patch should be easily disposed of after interrupting the power supply from the cell with a simple configuration.

In the above description, the liquid electrolyte solution is sealed between the outer case members 5 and 6. The electrolyte solution may also be a gel electrolyte solution. The use of the gel electrolyte solution makes it possible to produce the sheet-type air cell 10 in the printing process, thereby reducing the cost of the air cell 10. Moreover, the use of the gel electrolyte solution eliminates the liquid leakage from the air cell 10 and is also advantageous in, e.g., facilitating the configuration in which the power supply from the air cell is interrupted by cutting the power generation elements of the air cell, as will be described in detail later with reference to FIG. 6.

The cell used in the wearable patch 100 of this embodiment may be a known sheet-type cell such as a manganese cell other than the air cell if the cell capacity is sufficient to operate the wearable patch 100 for a desired time. Even a sheet-type cell other than the air cell can prevent the liquid leakage from the cell and have the advantage of cutting the power generation elements when the sheet-type cell does not include a liquid electrolyte solution in the outer case.

Moreover, the cell used in the wearable patch 100 of this embodiment may be a coin-type cell (button-type cell) other than the sheet-type cell. In such a case, a coin-type air cell, which is used as a power source of a hearing aid or the like, is preferred because it can be thinner and larger in cell capacity than the other coin-type cells.

[Drive Circuit Unit]

The drive circuit unit 20 may be composed of known thin film electronic circuit components, including, e.g., the following: wiring that is made of a metal thin film such as copper and formed on a film substrate; one or more electronic circuits (thin film chips) that function as a memory, a processor, a transmitting and receiving circuit, etc.; and an antenna element that is made of a metal thin film and used for communication with the outside. To avoid the complexity of the figures, the illustration of each constituent member of the drive circuit unit 20 is omitted.

As a matter of course, the function of the drive circuit unit 20 is designed to meet the purpose of the wearable patch 100. For example, the body temperature of the wearer can be measured in the following manner. The temperature of a sensor plate (which is the functional element 50, as will be described later) is detected by, e.g., a change in current flowing through the sensor plate, and the measured value of the body temperature is transmitted from the antenna element to a connected external device (e.g., smartphone) in accordance with a control signal from the external device or under the control of a logic circuit included in the drive circuit unit 20.

When the functional element 50 is a unit for injecting a drug solution into the wearer's body, the unit is controlled so that a predetermined amount of the drug solution is introduced into the skin of the wearer at a predetermined time by using the timer function of the drive circuit unit 20 or in accordance with an operation signal from the external device.

As described above, the connection terminals 21 are formed on the underside of the drive circuit unit 20. The power supply wires 31 are formed on the upper surface of the base 30 and connected to the two electrode terminals 9 of the sheet-type air cell 10, respectively. Thus, power is supplied from the air cell 10 to the electronic circuit components of the drive circuit unit 20 via the power supply wires 31.

[Base, Cover Member]

The wearable patch 100 of this embodiment includes the base 30 that defines the overall shape of the patch. The air cell 10 and the drive circuit unit 20 are formed on the upper surface of the base 30, and the functional element 50 and the adhesive layer 60 are formed on the lower surface of the base 30.

The base 30 may be, e.g., a sheet-type resin film with a thickness of about 20 to 500 μm. Examples of the resin film include a nylon film (such as a nylon 66 film) and a polyester film (such as a polyethylene terephthalate (PET) film). In the wearable patch 100 of this embodiment, the base 30 should not be too thick in order to be able to cut a predetermined portion of the wearable patch 100 with the minimum possible force for disposal. Specifically, the thickness of the resin sheet is more preferably 100 μm or less, and further preferably 50 μm or less.

The base 30 serves as a substrate that supports the entire wearable patch 100. Therefore, the thickness of the base 30 may be appropriately determined by the size, weight, etc. of the members that are formed on both surfaces of the base, e.g., depending on whether the air cell 10 to be mounted is a sheet-type cell or a coin-type cell or whether the functional element 50 is a sensor plate or a drug injection unit.

As shown in FIGS. 1 and 2, the wearable patch 100 of this embodiment includes a cover member 40 that covers the upper surface of the base 30. The cover member 40 mainly covers and protects the power supply wires 31 formed on the surface of the base 30. In particular, when the cell 10 is an air cell, the cover member 40 has an opening so as not to cover the air holes of the air cell.

FIGS. 1 and 2 show a configuration example in which the cover member does not cover the drive circuit unit 20. However, the drive circuit unit 20 may be covered with the cover member 40 so that the electronic circuit components are exposed to the surface of the drive circuit unit 20.

Similarly to the base 30, the cover member may be, e.g., a sheet-type resin film. Examples of the resin film include a nylon film (such as a nylon 66 film) and a polyester film (such as a polyethylene terephthalate (PET) film). The thickness of the cover member 40 may be 20 μm to 500 μm, which is the same as that of the base. However, unlike the base 30, the cover member 40 is not used as a substrate for the entire wearable patch 100. Therefore, the thickness of the cover member 40 is preferably as small as about 20 to 100 μm to reduce the weight of the wearable patch 100 and to facilitate the cutting process for disposal of the wearable patch 100, as will be described later.

The cover member 40 is not required if the cell 10, the drive circuit unit 20, and the conductive path that connects the cell 10 and the drive circuit unit 20 to supply power are not exposed to the outside due to their configurations and arrangements, e.g., where they are closely adjacent to each other without any space. In this regard, the cover member 40 is not an essential component of the wearable patch 100 of this embodiment.

[Functional Element]

The functional element 50 of the wearable patch 100 of this embodiment shown in FIGS. 1 and 2 is a thin film or a sensor plate in the form of a thin plate. For example, the functional element 50 may be a member that can detect biological information, including body temperature, pulse, respiratory rate, etc., by bringing it into direct contact with or in close proximity to the skin of the wearer. The functional element 50 does not necessarily have to be in direct contact with the skin of the wearer of the wearable patch 100, as shown in FIGS. 1 and 2. The functional element 50 may be in close proximity to the skin of the wearer via a thin sheet or the like to obtain the biological information.

The functional element 50 can be provided in various forms as long as it performs the intended function of the wearable patch 100. For example, the functional element 50 may be metal foil, a resin film on which a conductive member (metal or carbon) is formed, or a thin film formed on the lower surface of the base 30.

The functional element 50 and the drive circuit unit 20 are connected by, e.g., connection wires (not shown).

The functional element 50 is not limited to, e.g., the above sensor plate that acquires the physical information of the wearer, and may be any member having various functions such as a drug injection unit that injects a drug solution into the wearer's body at predetermined time intervals or a drug administration unit that supplies a transdermal drug to the surface of the skin with appropriate timing.

When the functional element 50 is an active member such as a drug injection unit or a drug administration unit, it requires a tank for containing drugs or a micro pump for delivering drugs. Therefore, the thickness of the functional element 50 is increased as compared to, e.g., the sensor plate. In such a case, an opening may be formed in the base 30, through which a part of the functional element 50 is located above the base 30 while maintaining the contact portion with the skin of the wearer. This configuration can prevent an increase in the thickness of the wearable patch 100.

[Adhesive Layer]

In the wearable patch 100 of this embodiment, the adhesive layer 60 is formed on the lower surface of the base 30 so as to surround the functional element 50.

The adhesive layer 60 is used in direct contact with the skin. Therefore, the adhesive layer 60 is made of a medically certified adhesive that has been proved not to cause a rash or irritation to the skin even if it sticks to the skin for at least a certain period of time.

The adhesive strength of the adhesive layer 60 is considered in view of the specifications (size, thickness, weight, etc.) of the wearable patch 100 and the mobility of the part of the human body to which the wearable patch 100 may be attached. Then, the material of the adhesive layer 60 is selected and the position and area of the adhesive layer 60 are determined.

[Cutting Start Portion]

As shown in FIG. 1, the wearable patch 100 of this embodiment has a substantially triangular cut 71 as a cutting start portion 70. The cut 71 is formed in the edge, e.g., one long side of the laminated portion of the base 30 and the cover member 40, where the adhesive layer 60 is not present on the lower surface of the base 30.

The tip of the cut 71 in the base 30 and the cover member 40 is directed to the power supply wires 31, which connect the cell 10 and the drive circuit unit 20 to supply power. Therefore, to dispose of the wearable patch 100, the user holds the two ends of the cut 71 and applies a force to twist the base 30, so that a crack occurs from the cut 71 and propagates through the base 30 and the cover member 40, tearing the wearable patch 100 into two parts along the extension of the cut 71. Thus, the power supply wires 31 can easily be cut. Consequently, the power supply from the cell 10 to the drive circuit unit 20 is interrupted, thereby ensuring that the operation of the drive circuit unit 20 is stopped.

The shape of the cut 71 of the cutting start portion 70, specifically the position of the vertex and the inclination angle between the two sides of the triangular cut 71 are determined so that the force required to cut the wearable patch 100 is 200 N or less. In this case, the force of 200 N means the load strength, i.e., the tear strength that can be measured with, e.g., a digital force gage "ZP-500N (trade name)" manufactured by IMADA CO., LTD.

If the tear strength is more than 200 N, it is rather difficult to tear the wearable patch 100. Therefore, the tear strength is set to be 200 N or less because adults, including women, can easily tear the wearable patch 100. The cut 71 can help the user to tear the wearable patch 100 with a force of 200 N or less, but would be useless if the wearable patch 100 is unnecessarily cut during use, e.g., when the wearable patch 100 is attached to the skin of the user. Thus, it is desirable that the strength of the wearable patch 100 is set so that the force required to cut the wearable patch 100 is 5 N or more.

In the above description, both the power supply wires 31, which are respectively connected to the positive electrode and the negative electrode of the cell 10, are cut by a crack developed from the cut 71 as a starting point. However, only one of the power supply wires 31 may be cut if the power supply from the cell 10 to the drive circuit unit 20 is reliably interrupted. In view of the arrangement of the power supply wires 31 on the base 30, the position of the cut 71 and the direction of a break line that starts from the cut 71 may be designed to reliably interrupt the power supply from the cell 10.

Similarly, it is not essential that the wearable patch 100 is divided into two parts by the break line starting from the cut 71. For example, the break line may extend about halfway across the width of the wearable patch 100. In other words, the break line may be partially generated in the wearable patch 100, provided that the power supply is interrupted by the disconnection of the conductive path from the cell 10 to the drive circuit unit 20, and the interruption of the power supply is maintained even if the two separate parts along the break line come close to each other to substantially restore the original shape of the wearable patch 100.

(Configuration Examples of Cutting Other Portions of the Wearable Patch Using the Cutting Start Portion)

Figure 5:
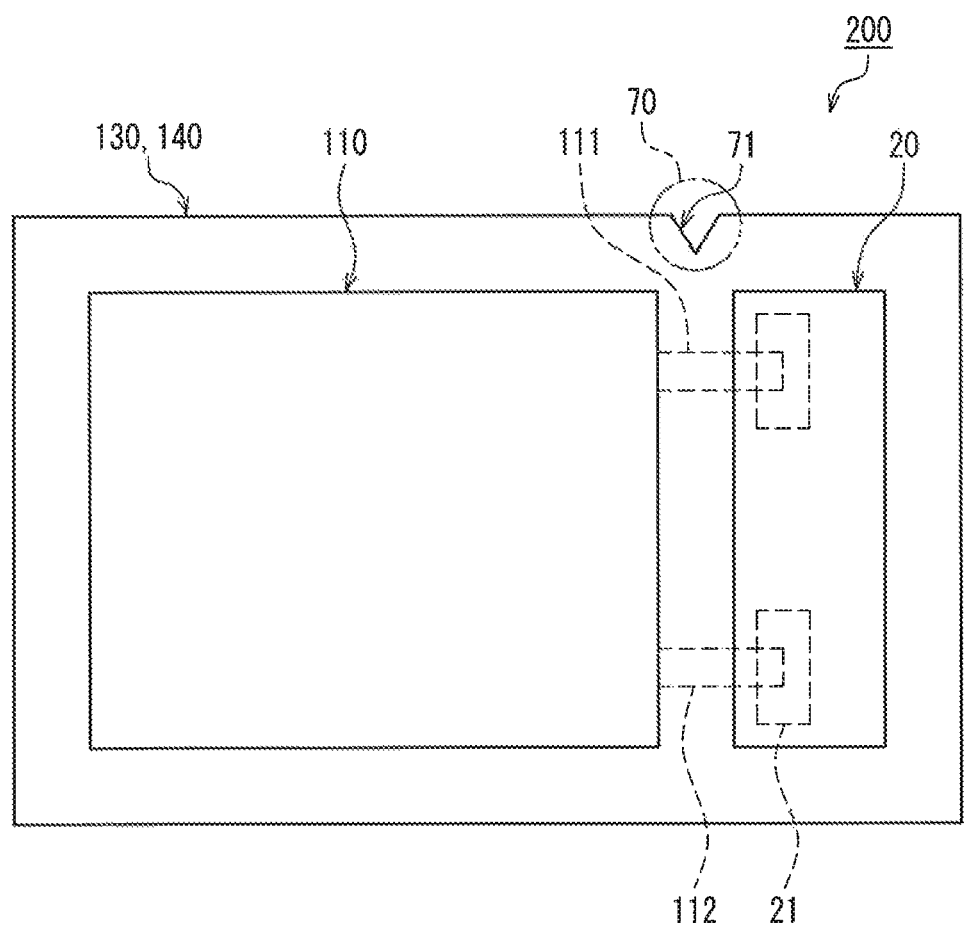
FIG. 5 is a plan view illustrating a second configuration example of a wearable patch of Embodiment 1.

FIG. 5 is a plan view illustrating a second configuration example of a wearable patch of this embodiment.

In the wearable patch 100 of this embodiment shown in FIG. 1, the cutting start portion 70 is formed in the edge and located near the conductive path 31, which connects the cell 10 and the drive circuit unit 20, and the power supply wires 31 can be cut with a force of 200 N or less along the break line starting from the cutting start portion 70.

A wearable patch 200 of the second configuration example in FIG. 5 differs from the wearable patch 100 in FIG. 1 in the following point. A sheet-type cell 110 is provided on a base 130 and has two electrode terminals (a positive electrode terminal 111 and a negative electrode terminal 112) that extend in the principal surface direction of the sheet-type cell 110 (i.e., extend to the right of FIG. 5). On the other hand, the sheet-type cell 10 has the electrode terminals 9 that are formed on the underside of the sheet-type cell 10.

In the wearable patch 200, the positive electrode terminal 111 and the negative electrode terminal 112 extending from the sheet-type cell 110 are directly connected to connection terminals 21 of a drive circuit unit 20, respectively, so that power is supplied from the cell 110 to the drive circuit unit 20. Although not shown in FIG. 5, a functional element 50, an adhesive layer 60, etc. are the same as those of the wearable patch 100 in FIG. 1. Therefore, the same members as those of the wearable patch 100 in FIG. 1 are denoted by the same reference numerals, and the detailed explanation will not be repeated.

The wearable patch 200 with the above configuration has a cut 71 as a cutting start portion 70. The cut 71 is formed in the edge of the laminated portion of the base 130 and a cover member 140 and is located in the region between the cell 110 and the drive circuit unit 20. A break line is generated from the cut 71 as a starting point and runs along the extension of the cut 71, thereby cutting the electrode terminals (111, 112) of the sheet-type cell 110.

Thus, the electrode terminals (111, 112) of the sheet-type cell 110 are cut along the break line starting from the cutting start portion 70. This configuration can also interrupt the power supply from the cell 110 to the drive circuit unit 20. Using the cutting start portion 70, the user can tear the wearable patch 200 with a force of 200 N or less and safely dispose of the wearable patch 200.

Only one of the two electrode terminals, i.e., the positive electrode terminal 111 and the negative electrode terminal 112 of the cell 110 may be cut if the power supply from the cell 110 is reliably interrupted. For example, unlike the example shown in FIG. 5, when the electrode terminals extending from the cell 110 are not arranged side by side, the cutting start portion 70 may be provided on the side of the base 130 where one of the two connection terminals is located. Similarly to the wearable patch 100, the wearable patch 200 can be cut with a force of 200 N or less along the break line starting from the cutting start portion 70, and does not need to be completely divided into two parts.

Figure 6:
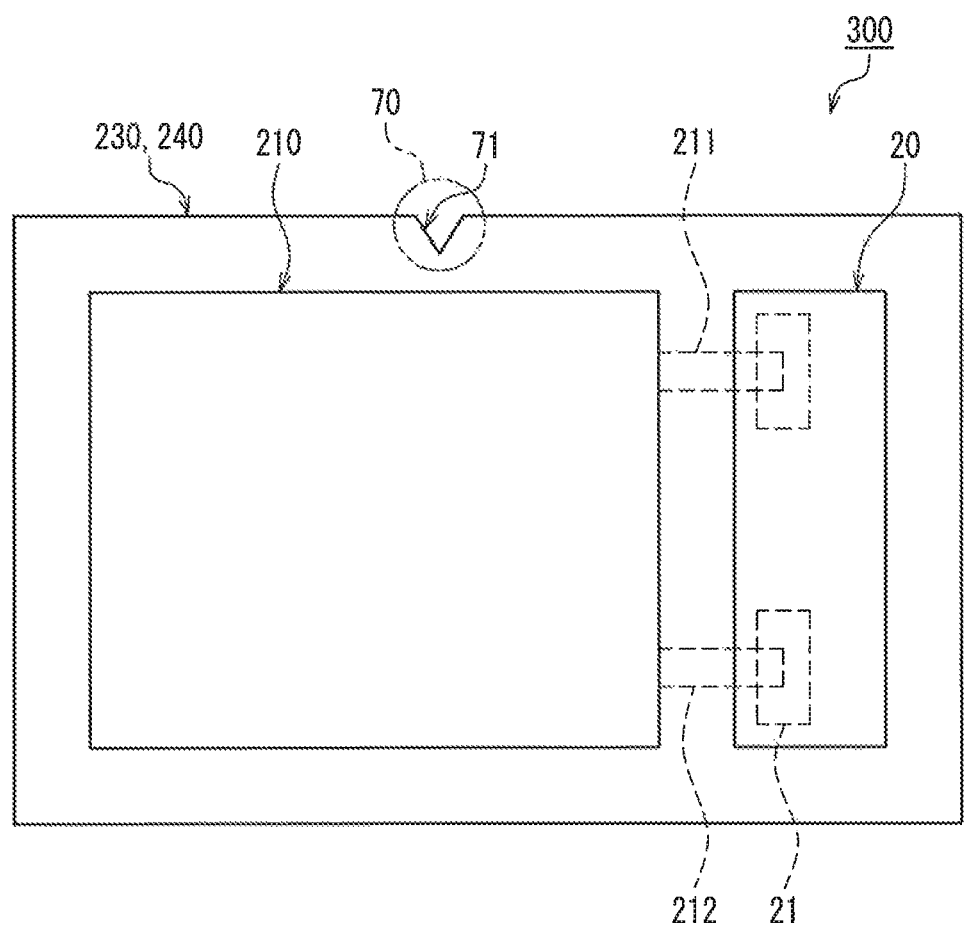
FIG. 6 is a plan view illustrating a third configuration example of a wearable patch of Embodiment 1.

FIG. 6 is a plan view illustrating a third configuration example of a wearable patch of this embodiment.

A wearable patch 300 of the third configuration example in FIG. 6 has a cut 71 as a cutting start portion 70. The cut 71 is formed in the edge of a base 230 and is located on the side of a substantially central portion of a sheet-type air cell 210, i.e., the portion of the cell 210 where the power generation elements such as a positive electrode and a negative electrode are provided.

Since the cut 71 of the cutting start portion 70 is located on the side of the power generation elements of the sheet-type cell 210, the power generation elements can be cut along a break line that is developed from the cut 71 as a starting point. This configuration can stop the power supply function of the cell and ensure that the operation of a drive circuit unit 20 is stopped. Thus, the wearable patch 300 can be disposed of safely.

Needless to say, cutting the power generation elements of the cell 210 along the break line starting from the cutting start portion 70, as shown in FIG. 6, cannot be applied to a wearable patch that includes a coin-type cell as an operating power source.

Moreover, such a configuration cannot also be applied to a wearable patch that includes a sheet-type cell, if the positive electrode and the negative electrode are made of, e.g., a thin metal plate and cannot be easily cut or if the electrolyte solution may leak due to damage to the cell. In view of these problems, the configuration in which the power generation elements of the cell are cut along the break line starting from the cutting start portion cannot always be used, depending on the configuration of the cell mounted on the wearable patch.

Although different from the configuration in FIG. 6, the power generation elements of the sheet-type cell may be cut along the break line starting from the cutting start portion so that the positive electrode and the negative electrode are divided into different parts. This configuration can be achieved, e.g., when the sheet-type cell 210 provided on the base 230 is rotated 90 degrees to the left in FIG. 6.

Consequently, the function of the sheet-type cell can be more reliably stopped.

In FIG. 6, the electrode terminals extend laterally from the sheet-type cell, which is the same configuration as that shown in FIG. 5. It goes without saying that cutting the power generation elements of the sheet-type cell along the break line starting from the cutting start portion 70 can also be applied to the sheet-type cell shown in FIG. 1, in which the electrode terminals are formed on the underside of the cell and connected to the connection terminals of the drive circuit unit by the power supply wires. Similarly to the first and second configurations, the force required to cut the wearable patch is 200 N or less in the third configuration in which the power supply is interrupted by cutting the power generation elements of the sheet-type cell.

As described above, in the wearable patch of Embodiment 1, the cutting start portion is formed in the edge, and the elements for supplying power from the cell to the drive circuit unit are cut along the break line starting from the cutting start portion.

Due to the presence of the cutting start portion, the user can easily tear the resin base of the wearable patch to reliably interrupt the power supply from the cell to the drive circuit unit with a force of 200 N or less, and thus can safely dispose of the wearable patch. In the absence of the cutting start portion, however, even if the base is thin and the cutting strength of the wearable patch itself is small, the wearable patch cannot be easily cut without using tools such as scissors.

In FIGS. 1 to 6, the wearable patch has a triangular cut as the cutting start portion. The cutting start portion of the wearable patch of this embodiment is not limited to a triangular cut and may be, e.g., a substantially semicircular cut in which the break line is generated from the inside rounded end, a semi-oval cut, a rectangular cut, or a liner cut.

The cutting start portion is not limited to the cut and may be a portion having a lower strength than the other portions. Such a cutting start portion can be formed in a portion of the edge of the base by, e.g., reducing the thickness of the portion, using a low strength material for the portion, or deforming the portion by pressing it in the thickness direction. It is preferable that the cutting start portion is colored with different colors or marked with, e.g., an arrow so that the user can clearly identify the position of the cutting start portion.

Although not shown in the figures, a low strength portion may be provided on the extension of the cut of the cutting start portion. In the low strength portion, e.g., the thickness of the base or the cover member is reduced as compared to the other portions. This configuration can make it easier to tear the wearable patch.

Embodiment 2

Next, a wearable patch of Embodiment 2 will be described. The wearable patch of this embodiment includes a cut tape as a cutting facilitating member that allows a predetermined portion of the wearable patch to be cut with a force of 200 N or less.

Figure 7:
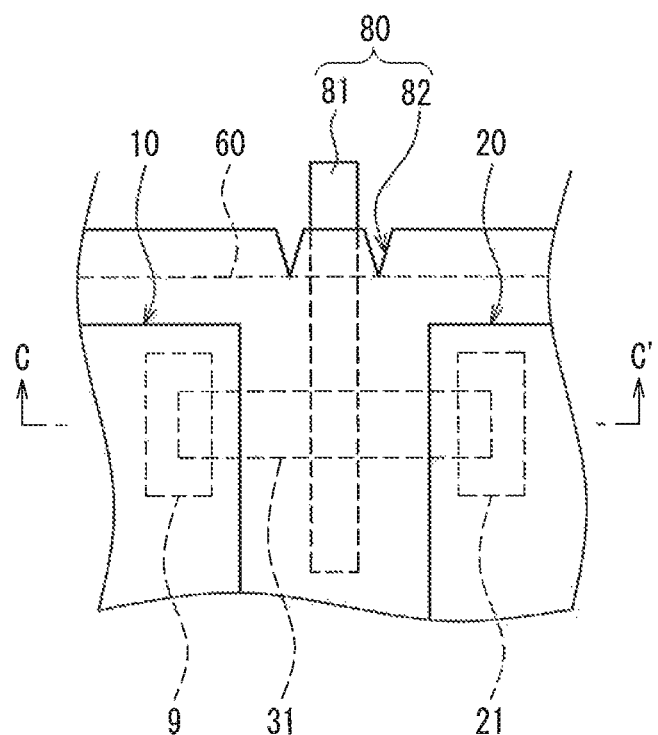
FIG. 7 is an enlarged plan view illustrating the main part of the configuration of a wearable patch of Embodiment 2.

FIG. 7 is an enlarged plan view illustrating the main part of the configuration of the wearable patch of Embodiment 2.

Figure 8:
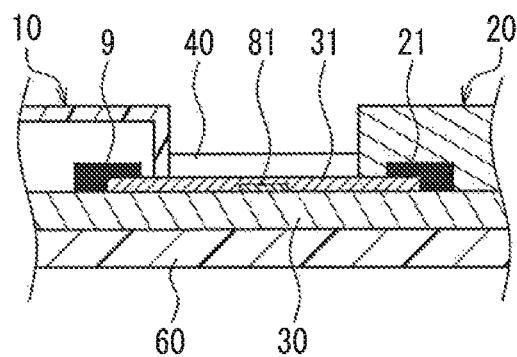
FIG. 8 is an enlarged cross-sectional view illustrating the main part of the configuration of a wearable patch of Embodiment 2.

FIG. 8 is an enlarged cross-sectional view illustrating the main part of the configuration of the wearable patch of Embodiment 2.

The wearable patch shown in FIGS. 7 and 8 is the same as the wearable patch 100 shown in FIGS. 1 and 2 in the configuration (i.e., the cell, the drive circuit unit, the base, the cover member, the functional element, and the adhesive layer) except for the cut tape as the cutting facilitating member. Therefore, the same members as those of the wearable patch 100 in FIG. 1 are denoted by the same reference numerals, and the detailed explanation will not be repeated. FIGS. 7 and 8 are enlarged views of the power supply wire 31 (conductive path) that electrically connects the cell 10 and the drive circuit unit 20 of the wearable patch.

As shown in FIGS. 7 and 8, the wearable patch of Embodiment 2 includes a cut tape 81 as a cutting facilitating member 80. Specifically, the cut tape 81 is located under the power supply wire 31 that connects the electrode terminal 9 of the cell 10 and the connection terminal 21 of the drive circuit unit 20 between the base 30 and the cover member 40 of the wearable patch.

One end of the cut tape 81 is exposed to the side (edge) of the wearable patch. When the user holds this exposed portion and pulls the cut tape 81 up toward the cover member 40, the user can easily cut the power supply wire 31 and the cover member 40 because they are placed on the cut tape 81. Thus, the power supply wire 31 (conductive path) is cut, so that the power supply from the cell 10 to the drive circuit unit 20 can be interrupted.

As shown in FIG. 7, small notches 82 are formed on both sides of the position at which the end of the cut tape 81 is located. This configuration can make it easier to cut the cover member 40 when the cut tape 81 is pulled up, and thus can reliably cut the power supply wire 31.

In FIG. 7, the end of the cut tape 81 protrudes from the side of the wearable patch. The end of the cut tape 81 may be located on the long side of the wearable patch rather than protruding from it. In this case, it is desirable that at least the width of the cover member 40 at the position of the cut tape 81 should be reduced so that the user can easily grab the end of the cut tape 81.

The cut tape may be made of a resin material or a paper material. The cut tape may be in the form of a wire other than a ribbon, as shown in FIGS. 7 and 8. Moreover, the cut tape may also be made of a metal material. In such a case, however, the cut tape should be insulated from the power supply wire 31 to be cut, and the shape and arrangement of the cut tape should be determined not to interfere with the function of the wearable patch. Further, when the end of the cut tape protrudes from the side of the wearable patch, and this patch is attached to the skin of the user, care should be taken not to injure the user. Whatever the material, the cut tape needs to be designed to have a higher breaking strength than the cover member 40 and the power supply wire 31 of the wearable patch, thereby avoiding the situation in which the power supply wire 31 cannot be cut because the cut tape 81 is broken as it is pulled up.

In the wearable patch of Embodiment 2, the power supply wire 31 (conductive path) can be cut with a force of 200 N or less by using the cut tape 81 as the cutting facilitating member.

In FIGS. 7 and 8, the cut tape 81 (cutting facilitating member) is used to cut the power supply wire 31 that connects the cell 10 and the drive circuit unit 20 of the wearable patch. However, the use of the cut tape 81 is not limited to the cutting of the power supply wire (conductive path), and the cut tape 81 may be used to cut the electrode terminals of the cell, as described in Embodiment 1 with reference to FIG. 5. Moreover, the cut tape 81 may also be used to cut the power generation elements of the sheet-type cell 10, as described in Embodiment 1 with reference to FIG. 6.

In FIG. 7, only one of the two power supply wires 31, which connect the electrode terminals 9 of the cell 10 and the connection terminals 21 of the drive circuit unit 20, that is, the power supply wire 31 located on the upper side of the figure is cut.

However, the cut tape 81 may be configured to cut the two power supply wires 31 together.

Embodiment 3

Next, a wearable patch of Embodiment 3 will be described. The wearable patch of this embodiment includes a cutting portion as a cutting facilitating member that allows a predetermined portion of the wearable patch to be cut with a force of 200 N or less.

Figure 9:
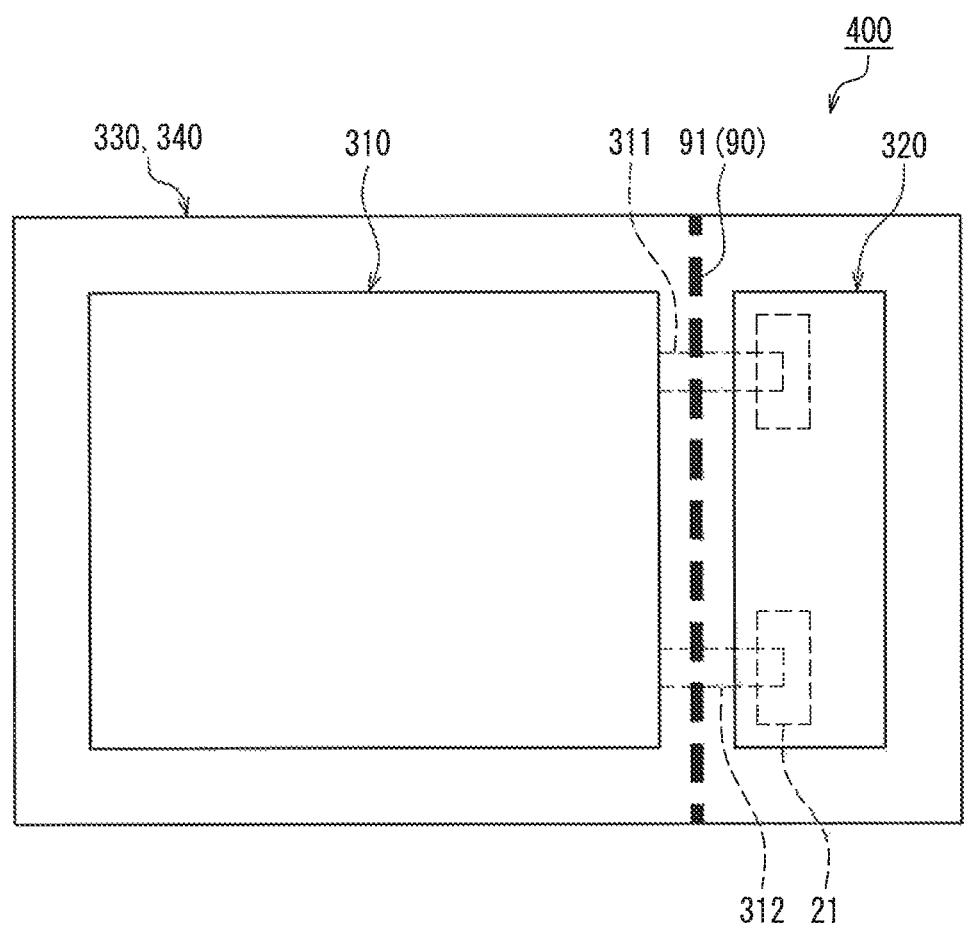
FIG. 9 is a plan view illustrating the configuration of a wearable patch of Embodiment 3.

FIG. 9 is a plan view illustrating the configuration of the wearable patch of Embodiment 3.

A wearable patch 400 of Embodiment 3 has a cutting portion 90, which itself can easily be cut. When the user disposes of the wearable patch 400, the cutting portion 90 can be cut to interrupt the power supply from a cell 310 to a drive circuit unit 320.

As shown in FIG. 9, perforations 91 are made as the cutting portion 90 in a base 330 and a cover member 340 of the wearable patch 400.

Since the perforations 91 are made in the base 330 and the cover member 340 that form the entire wearable patch 400, the wearable patch 400 can be torn more easily. Upon cutting the base 330 and the cover member 340, electrode terminals (311, 312) of the cell 310, which are provided between the base 330 and the cover member 340, are cut simultaneously, so that the power supply from the cell 310 to the drive circuit unit 320 can be interrupted.

In FIG. 9, the electrode terminals extend laterally from the cell, as described in Embodiment 1 with reference to FIGS. 5 and 6. The perforations 91 of the cutting portion 90 can also be applied to the configuration in which the electrode terminals are formed on the underside of the cell and connected to the connection terminals of the drive circuit unit by the power supply wires (conductive path). In this case, the perforations 91 may be made in the portion where the power supply wires are provided.

On the other hand, the perforations are through holes that penetrate the wearable patch in the thickness direction. Therefore, it is generally difficult to use the perforations as the cutting portion of the wearable patch when the power generation function of the cell is stopped by cutting the power generation elements.

However, when the wearable patch includes an air cell, air holes are usually formed in the outer case member located on the positive electrode side. These air holes may be utilized, i.e., their shape and arrangement may be adjusted so that the power generation elements of the cell can be cut with a force of 200 N or less.

In the wearable patch of Embodiment 3 shown in FIG. 9, the perforations 91 of the cutting portion 90 are used as the cutting facilitating member. This configuration also allows the wearable patch 400 to be cut with a force of 200 N or less.

As the cutting facilitating member of the wearable patch of Embodiment 3, the cutting portion is not limited to the perforations shown in FIG. 9. For example, the cutting portion (which itself can easily be cut) may be formed by reducing the thickness of the base or the cover member or may be made of a material weaker than that of the other portions. Thus, the cutting portion can be cut with a small force, as compared to the other portions.

In this case, the cutting portion other than the perforations is preferably colored or printed with a dotted line, which appears to correspond to perforations, so that the user can easily identify the cutting portion and applies a force to cut the cutting portion correctly.

As described above, the wearable patch of the present application has the cutting facilitating member that allows the wearable patch to be cut with a force of 200 N or less. The cutting facilitating member makes it easier to cut the members for supplying power from the cell to the drive circuit unit in the wearable patch.

Accordingly, the user can easily tear the wearable patch to interrupt the power supply from the cell to the drive circuit unit, which causes the drive circuit unit to stop operating. Consequently, the user can safely dispose of the wearable patch.

In each of the wearable patches of the above embodiments, the cell and the drive circuit unit are next to each other on the base. However, the wearable patch of the present application is not limited to this configuration.

For example, the cell and the drive circuit unit may be stacked in the thickness direction. Alternatively, the cell, the drive circuit unit, and the functional element may be stacked in the thickness direction. These configurations can provide compact wearable patches with a small surface area. Even the compact wearable patches can be disposed of safely by using the cutting facilitating member that allows any of the following portions to be cut with a force of 200 N or less: the conductive path that connects the cell and the drive circuit unit; the electrode terminals of the cell; and the power generation elements of the cell.

When a wearable patch has a compact layered structure, a plurality of members of the wearable patch will be cut at once by the cutting facilitating member, and thus the drive circuit unit can be more reliably stopped. On the other hand, a further increase in the thickness of the wearable patch can make it difficult to cut the wearable patch with a force of 200 N or less. In this case, the wearable patch can be cut with a force of 200 N or less, e.g., by combining two or more cutting facilitating members in the above embodiments (such as the combination of the cut and the cut tape) or by using any of the cutting facilitating members in combination with a means for reducing the strength (e.g., the thickness) of a portion of the wearable patch that is to be actually cut.

Although not mentioned in the above description, the wearable patch including an air cell requires a sealing member to cover the air holes of the air cell before operating the wearable patch. Moreover, the wearable patch requires a release sheet that covers the surface of the adhesive layer to protect it before attaching the wearable patch to the skin of the wearer. Any known materials can be suitably used as the protective sheet and the release sheet.

In the above embodiments, the wearable patch is attached to the body by the adhesive force of the adhesive layer of the wearable patch. The method for attaching the wearable patch to the person to be measured is not limited to the adhesive layer. For example, the wearable patch may be fastened to the body by using a belt or a cover film that covers the entire wearable patch.

<Embodiments of Sheet-Type Cell Disclosed in the Present Application>

Next, embodiments of a sheet-type cell disclosed in the present application will be described.

A sheet-type cell of the present application can be mounted on the wearable patch as an operating power source. Moreover, the sheet-type cell can be used for a wide range of applications such as power sources of various portable devices by taking advantage of its small thickness.

Similarly to the above wearable patch, the sheet-type cell has the cutting facilitating member and can be cut with a force of 200 N or less. Therefore, during actual use of the sheet-type cell in the medical field or the home, the power supply from the cell is reliably interrupted, so that the cell can be disposed of safely.

Embodiment 4

A sheet-type cell of Embodiment 4 includes a cutting start portion as a cutting facilitating member.

Figure 10:
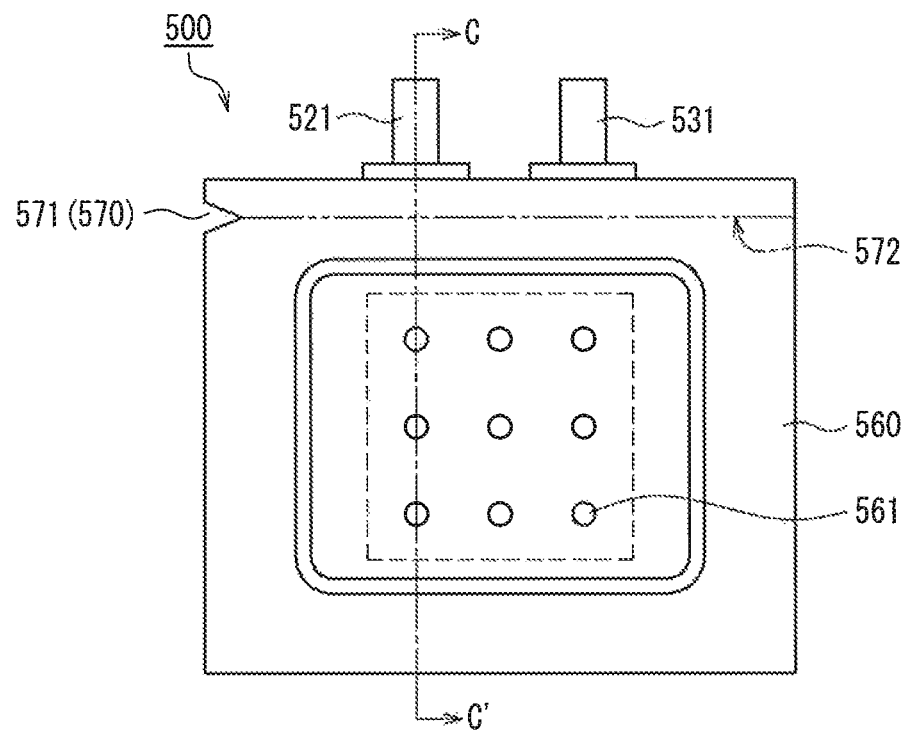
FIG. 10 is a plan view illustrating the schematic configuration of a sheet-type cell of Embodiment 4.
Figure 11:
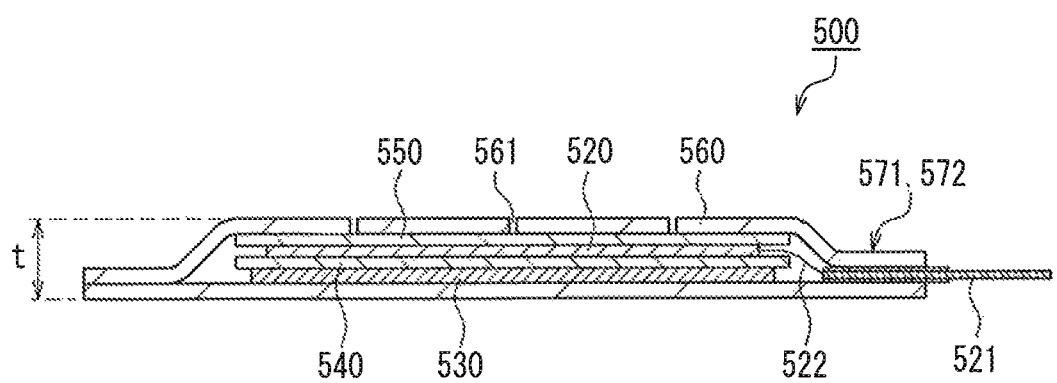
FIG. 11 is a cross-sectional view illustrating the schematic configuration of a sheet-type cell of Embodiment 4.

FIGS. 10 and 11 show a configuration example of the sheet-type cell of the present application. FIG. 10 is a plan view illustrating one side of the sheet-type cell.

FIG. 11 is a cross-sectional view taken along the line C-C' in FIG. 10.

The sheet-type cell of this embodiment shown in FIGS. 10 and 11 is a sheet-type air cell.

As shown in FIG. 11, a sheet-type cell 500 includes a positive electrode 520, a separator 540, a negative electrode 530, and an electrolyte (not shown) that are contained in a sheet-type outer case 560. The positive electrode 520 is electrically connected to a positive electrode terminal 521 via a lead 522 in the cell 500. Although not shown in FIG. 10, the negative electrode 530 is also electrically connected to a negative electrode terminal 531 via a lead in the cell 500. As shown in FIGS. 10 and 11, the positive electrode terminal 521 and the negative electrode terminal 531 are drawn from the peripheral portion (corresponding to the edge of the sealed portion) of the sheet-type outer case 560 to the outside. In FIG. 10, the dotted line indicates the size of a catalyst layer of the positive electrode 520 contained in the sheet-type outer case 560.

The sheet-type outer case 560 has a plurality of air holes 561 at one side, where the positive electrode 520 is provided, to take air into the positive electrode.

Moreover, as shown in FIG. 11, a water repellent membrane 550 for preventing leakage of the electrolyte through the air holes 561 is provided on the surface of the positive electrode 520 that faces the sheet-type outer case 560.

The positive electrode 520 has a catalyst layer and may have, e.g., a laminated structure of the catalyst layer and the current collector. For the purpose of brevity, the individual layers of the positive electrode 520 are not distinguished from each other in FIG. 11.

The sheet-type cell 500 has a cut 571 as a cutting start portion 570. The cut 571 is formed in the side of the sealed portion (the peripheral portion) of the sheet-type outer case 560 near the positive electrode terminal 521 and the negative electrode terminal 531. When the cut 571 serves as a starting point, a portion between the cut 571 and the opposite side of the outer case 560 (indicated by an alternate long and two short dashes line in FIG. 10) is a low strength portion 572 with a tear strength of 200 N or less.

As described above, the sheet-type cell 500 of Embodiment 4 has the cutting facilitating member including the cut 571 of the cutting start portion 570 and the low strength portion 572 that is on the extension of the cut 571.

If there is no starting point for cutting such as the cut 571, the force required to start tearing the sheet-type cell will be more than 200 N even though the sheet-type cell has the low strength portion 572 with a tear strength of 200 N or less. Consequently, the sheet-type cell may not be torn, or a portion different from the intended portion is likely to be cut. Therefore, it is preferable that a starting point for cutting such as the cut 571 is formed to facilitate the tearing of the sheet-type cell.

In the sheet-type cell shown in FIG. 10, the low strength portion 572 with a tear strength of 200 N or less is preferably present in the sealed portion where at least one of the positive electrode terminal 521 and the negative electrode terminal 531 is provided. In this case, when the cell is torn and broken, at least one of the positive electrode terminal 521 and the negative electrode terminal 531 can be separated from the main body of the corresponding electrode. Thus, the torn piece of the cell with the remaining power generation elements will lose the terminal for supplying power to the outside (i.e., at least one of the positive electrode terminal and the negative electrode terminal). With this configuration, the cell loses its function by breakage (tearing) even if the cell capacity is left when the cell is broken. Therefore, the cell can be disposed of more safely.

In FIG. 10, the positive electrode terminal and the negative electrode terminal are drawn from the sealed portion on the same side of the sheet-type outer case. However, depending on the intended use of the cell, the positive electrode terminal and the negative electrode terminal may be drawn from different sides of the sheet-type outer case. In such a cell, the low strength portion with a tear strength of 200 N or less may be present in the sealed portion where either the positive electrode terminal or the negative electrode terminal is provided. When this cell is torn, one of the positive electrode and the negative electrode of the power generation elements that remain in the torn piece of the cell will lose the power supply terminal, so that power cannot be extracted to the outside.

To prevent the extraction of power from the power generation elements of the cell, the cell does not necessarily have to be torn into two pieces. The cell may lose its function by cutting at least one of the lead that connects the positive electrode terminal to the positive electrode and the lead that connects the negative electrode terminal to the negative electrode, while the original shape of the cell is substantially maintained.

Figure 12:
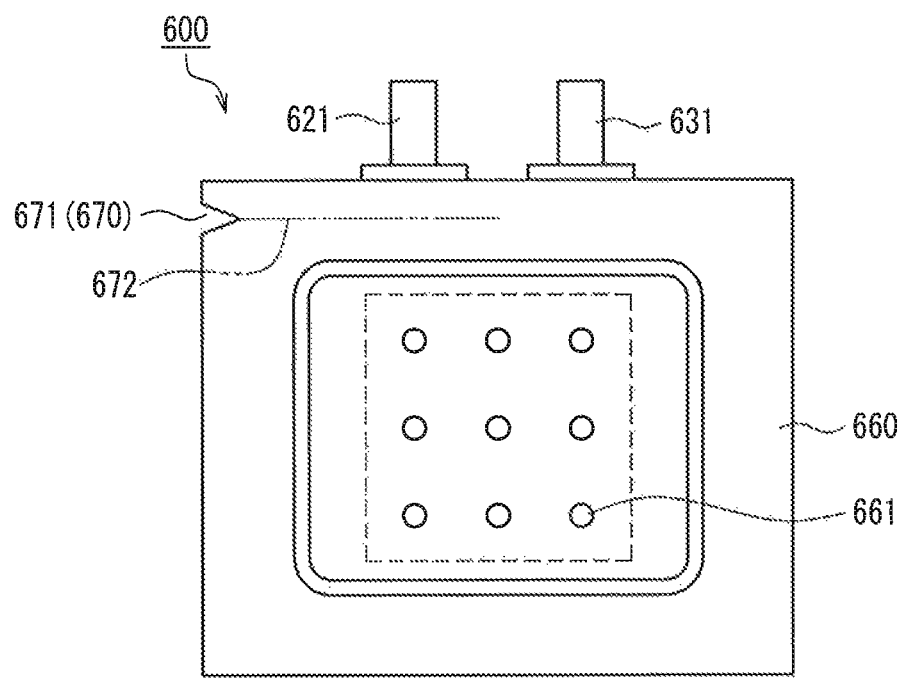
FIG. 12 is a plan view illustrating a second configuration example of a sheet-type cell of Embodiment 4.

FIG. 12 is a plan view schematically illustrating a second configuration example of the sheet-type cell of the present application.

A sheet-type cell 600 shown in FIG. 12 is also an example of an air cell. As shown in FIG. 12, the sheet-type air cell 600 has a cut 671 as a cutting start portion 670. For example, a low strength portion 672 is on the extension of the cut 671 and reaches only the position between a positive electrode terminal 621 and a negative electrode terminal 631. Even in this configuration, the lead that connects the positive electrode terminal 621 to the positive electrode can be cut by the low strength portion 672. In such a case, the positive electrode terminal 621 is not divided into a separate piece, but continues to be held by an outer case 660. However, this makes it possible to interrupt the power supply from the cell to the outside for disposal.

Figure 13:
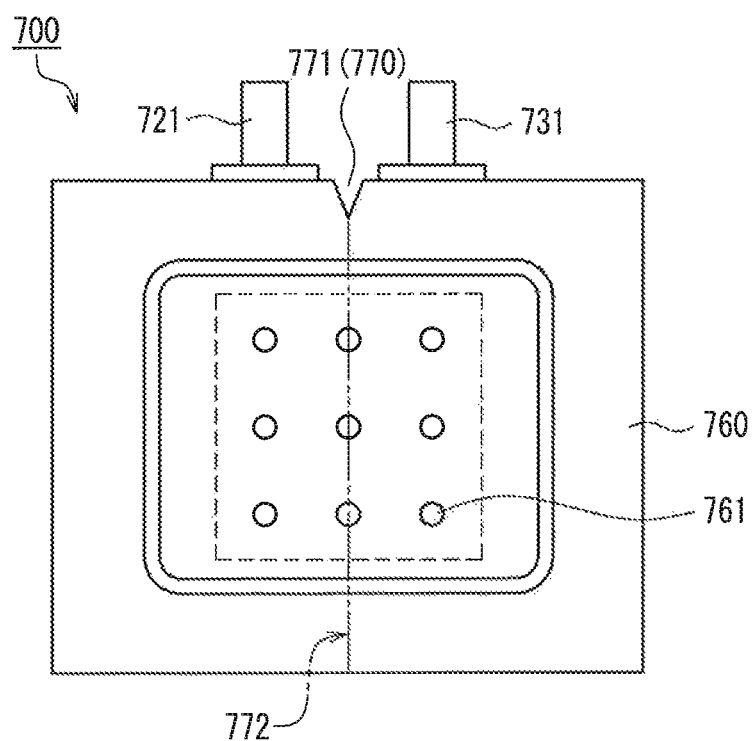
FIG. 13 is a plan view illustrating a third configuration example of a sheet-type cell of Embodiment 4.

FIG. 13 is a plan view schematically illustrating a third configuration example of the sheet-type cell of the present application.

A sheet-type cell 700 shown in FIG. 13 is also an example of an air cell. As shown in FIG. 13, the sheet-type air cell 700 has a cut 771 as a cutting start portion 770. The cut 771 is formed in the sealed portion of a sheet-type outer case 760 between the position at which a positive electrode terminal 721 is provided (drawn) and the position at which a negative electrode terminal 731 is provided (drawn). When the cut 771 serves as a starting point, a portion between the cut 771 and the opposite side of the outer case 760 (indicated by an alternate long and two short dashes line in FIG. 13) is a low strength portion 772 with a tear strength of 200 N or less. The sheet-type air cell 700 has the cutting facilitating member including the cut 771 and the low strength portion 772. When the sheet-type air cell 700 is torn by the cut 771 and the low strength portion 772, the power generation elements of the cell can be separated into two parts, and thus divided into the piece with the positive electrode terminal 721 and the piece with the negative electrode terminal 731.

As shown in FIG. 13, it is also preferable that the low strength portion with a tear strength of 200 N or less is present in the portion where the sheet-type cell can be torn into two pieces, i.e., the torn piece containing the positive electrode terminal and the torn piece containing the negative electrode terminal. In this case, the individual torn pieces have only one of the two connection terminals that connect the respective electrodes to the outside. Therefore, power cannot be extracted to the outside even if the cell capacity is left. With this configuration, the cell loses its function by breakage (tearing), and thus can be disposed of more safely.

As described above, the sheet-type cell of Embodiment 4 has the cutting facilitating member including the cut of the cutting start portion and the low strength portion that is on the extension of the cut. The cut and the low strength portion are formed in the sealed portion. With this configuration, the user can tear the sheet-type cell with a force of 200 N or less for disposal. Consequently, it is possible to interrupt the power supply from at least one of the positive electrode terminal and the negative electrode terminal of the sheet-type cell to the outside. Thus, the cell can be disposed of safely even if the power generation elements are still able to supply power.

In this embodiment, the sheet-type cell has a triangular cut as the cutting start portion. The shape of the cut is not limited to a triangle, and the cut may be in various forms such as a substantially semicircular cut, a semi-oval cut, a rectangular cut, and a liner cut. The cutting start portion is not limited to the cut and may be a portion having a lower strength than the other portions. Such a cutting start portion can be formed in the sealed portion of the sheet-type cell by, e.g., reducing the thickness of the portion, using a low strength material for the portion, or deforming the portion by pressing it in the thickness direction. It is preferable that the cutting start portion is colored with different colors or marked with, e.g., an arrow so that the user can clearly identify the position of the cutting start portion.

Further, when the user can tear the sheet-type cell with a force of 200 N or less, the sheet-type cell may include only the cutting start portion and eliminate the low strength portion that is on the extension of the cut.

Embodiment 5

A sheet-type cell of Embodiment 5 includes a cut tape as a cutting facilitating member.

Figure 14:
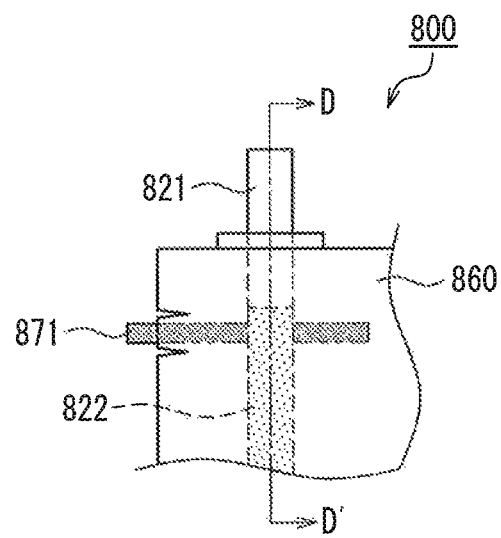
FIG. 14 is an enlarged plan view illustrating the main part of the configuration of a sheet-type cell of Embodiment 5.

FIG. 14 is an enlarged plan view illustrating the main part of the configuration of the sheet-type cell of Embodiment 5.

Figure 15:
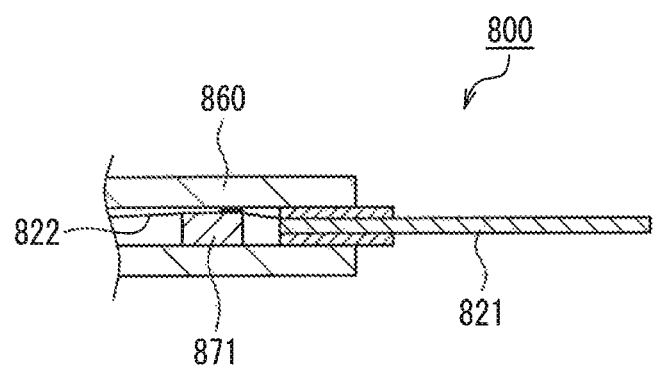
FIG. 15 is an enlarged cross-sectional view illustrating the main part of the configuration of a sheet-type cell of Embodiment 5.

FIG. 15 is an enlarged cross-sectional view illustrating the main part of the configuration of the sheet-type cell of Embodiment 5. FIG. 15 shows the cross section of a portion taken along the line D-D' in FIG. 14.

FIGS. 14 and 15 are enlarged views of the portion of a sheet-type outer case 860 of a sheet-type cell 800 of Embodiment 5, where a lead 822 connects a positive electrode (not shown) as a power generation element to a positive electrode terminal 821. In FIG. 14, a dotted line represents a part of the positive electrode terminal 821 and the lead 822, and an alternate long and two short dashes line represents a cut tape 871 provided inside the sheet-type outer case 860.

In the sheet-type cell 800 shown in FIGS. 14 and 15, the cut tape 871 (cutting facilitating member) is inserted in the sealed portion of the sheet-type outer case 860 where the positive electrode terminal 821 is provided. As shown in FIG. 15, the cut tape 871 is located under the lead 822 that connects the positive electrode to the positive electrode terminal 821. Since the sheet-type outer case 860 is composed of two outer case members that are joined together in the sealed portion, when the cut tape 871 is pulled up, the upper outer case member is torn off along with the lead 822 of the positive electrode, so that the conductive connection between the positive electrode and the positive electrode terminal 821 can be interrupted.

In FIGS. 14 and 15, the cut tape is used to cut the lead that conductively connects the positive electrode to the positive electrode terminal. However, the sheet-type cell of this embodiment is not limited to this configuration. The cut tape may be used to cut the lead that connects the negative electrode to the negative electrode terminal. Alternatively, the cut tape may be used to cut the two leads that are connected to the positive electrode terminal and the negative electrode terminal, respectively. Moreover, the cut tape may also be configured to cut the positive electrode terminal and/or the negative electrode terminal rather than the lead that connects the positive electrode or the negative electrode to the corresponding connection terminal.

As shown in FIG. 14, small notches are formed on both sides of the position at which the end of the cut tape 871 is located. This configuration can make it easier to cut the outer case 860 when the cut tape 871 is pulled up, and thus can reliably cut the lead 822.

In FIG. 14, the end of the cut tape 871 protrudes from the side of the sheet-type cell 800. The end of the cut tape 871 may be located so as not to protrude from the long side of the sheet-type cell 800. In this case, it is desirable that at least the width of the outer case 860 at the position of the cut tape 871 should be reduced so that the user can easily grab the end of the cut tape 871.

Embodiment 6

A sheet-type cell of Embodiment 6 includes a cutting portion that can easily be cut as a cutting facilitating member.

Figure 16:
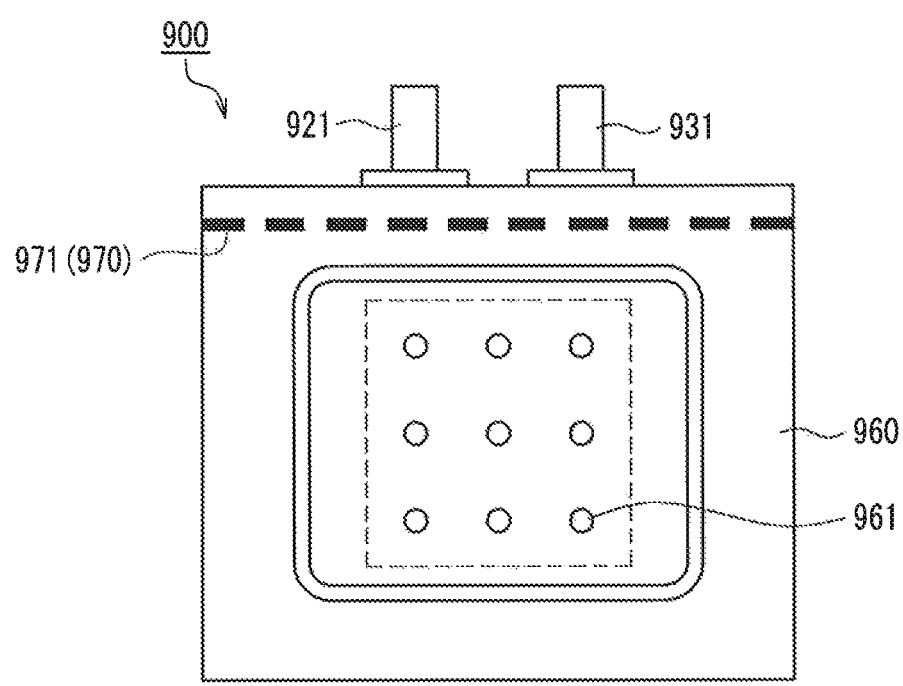
FIG. 16 is a plan view illustrating the configuration of a sheet-type cell of Embodiment 6.

FIG. 16 is a plan view of the sheet-type cell of Embodiment 6.

A sheet-type cell 900 of Embodiment 6 has a cutting portion 970, which itself can easily be cut. When the user disposes of the sheet-type cell 900, the cutting portion 970 can be cut to interrupt the power supply from the cell to the outside.

As shown in FIG. 16, perforations 971 are made as the cutting portion 970 in a sheet-type outer case 960 of the sheet-type cell 900 of Embodiment 6. Since the perforations 971 are made in the sealed portion of the outer case 960 of the sheet-type cell 900, the user can tear the outer case 960 with a force of 200 N or less. Upon cutting the outer case 960, leads that connect a positive electrode and a negative electrode to their respective electrode terminals (921, 931) are cut, so that the power supply from the cell to the outside can be interrupted.

In FIG. 16, the electrode terminals of the cell are arranged side by side on the same side of the sealed portion, as described in Embodiment 4 with reference to FIG. 10 or the like. When the two electrode terminals are provided on different sides of the outer case, the perforations may be made only in the portion where the lead is provided that connects one of the electrodes to the corresponding electrode terminal.

As the cutting facilitating member of the sheet-type cell of Embodiment 6, the cutting portion is not limited to the perforations shown in FIG. 16. For example, the cutting portion (which itself can easily be cut) may be formed by reducing the thickness of the base or the cover member or may be made of a material weaker than that of the other portions. Thus, the cutting portion can be cut with a small force, as compared to the other portions. In particular, the low strength portion of the sheet-type cell of Embodiment 4 corresponds to the cutting portion as the cutting facilitating member of this embodiment.

When the sheet-type cell includes the cutting portion other than the perforations, it is preferable that the cutting portion is colored or printed with a dotted line corresponding to perforations so that the user can easily identify the cutting portion and applies a force to cut the cutting portion correctly.

As described above, the sheet-type cell of the present application has the cutting facilitating member that allows a predetermined portion of the sheet-type cell to be cut with a force of 200 N or less. Thus, the power supply from the cell to the outside can be interrupted and the cell can be disposed of safely.

(Configuration of Sheet-Type Cell)

Hereinafter, the basic configuration of the sheet-type cell in Embodiments 4 to 6 will be described. The above sheet-type air cell that is mounted on the wearable patch of the present application as an operating power source can also be used for the sheet-type cell of the present application. The following is additional information about the configuration of the above sheet-type air cell.

The outer case of the sheet-type cell is a sheet-type outer case made of a resin film.

The resin film may be either a uniaxially oriented film or a biaxially oriented film. The uniaxially oriented film is likely to be torn in a particular direction. By taking advantage of this property, the sheet-type cell including the uniaxially oriented film can have a low strength portion with a tear strength of 200 N or less.

When the sheet-type cell is other than an air cell and is, e.g., an alkaline cell, a manganese cell, or a nonaqueous electrolyte cell, the positive electrode may have a structure in which a positive electrode mixture layer containing, e.g., a positive electrode active material, a conductive assistant, and a binder is formed on one side or both sides of a current collector.

When the sheet-type cell is an alkaline cell, examples of the positive electrode active material include silver oxides (such as silver (I) oxide and silver (II) oxide), manganese oxides such as manganese dioxide, nickel oxyhydroxide, and composite oxides of silver and cobalt, nickel, or bismuth. When the sheet-type cell is a manganese cell, examples of the positive electrode active material include manganese oxides such as manganese dioxide.

When the sheet-type cell is a nonaqueous electrolyte cell, examples of the positive electrode active material include the following: manganese dioxide; sulfides such as vanadium oxide, niobium oxide, titanium oxide, and iron disulfide; graphite fluoride; and various types of lithium-containing composite oxides including, e.g., lithium-containing manganese oxides such as $Li_xMn_3O_6$ (0<x<2) and $Li_xMnO_2$ (0<x<1), composite oxides having a spinel structure such as $Li_xTiO_{5/3}O_4$ (4/3≤x<7/3) and $LiMn_2O_4$ or a composite oxide obtained by substituting a part of the elements of $LiMn_2O_4$ with another element, lithium-containing composite oxides having a layered structure expressed as $L_{1+x}MO^1{}_2$ (−0.1<x<0.1, $M^1$: Co, Ni, Mn, Al, Mg, etc.), and olivine-type compounds expressed as $LiM^2PO_4$ ($M^2$: Co, Ni, Mn, Fe, etc.).

Examples of the lithium-containing composite oxides having the layered structure include the following: lithium cobaltate such as $LiCoO_2$; $LiN_{1-a}Co_{a-b}Al_bO_2$ (0.1≤a≤0.3, 0.01≤b≤0.2); and oxides containing at least Co, Ni, and Mn (such as $LiMn_{1/3}Ni_{1/3}Co_{1/3}O_2$, $LiMn_{5/12}Ni_{5/12}Co_{1/6}O_2$, and $LiNi_{3/5}Mn_{1/5}Co_{1/5}O_2$).

Examples of the conductive assistant of the positive electrode mixture layer include the following: carbon blacks such as acetylene black, Ketjenblack, channel black, furnace black, lamp black, and thermal black; carbon materials such as carbon fibers; conductive fibers such as metallic fibers; carbon fluoride; metal powders of copper, nickel, etc.; and organic conductive materials such as polyphenylene derivatives.

Examples of the binder of the positive electrode mixture layer include the following: polyvinylidene fluoride (PVDF), polytetrafluoroethylene (PTFE), styrene-butadiene rubber (SBR), carboxymethyl cellulose (CMC), and polyvinyl pyrrolidone (PVP).

In the composition of the positive electrode mixture layer, the amount of the positive electrode active material is preferably 80 to 98% by mass, the content of the conductive assistant is preferably 1.5 to 10% by mass, and the content of the binder is preferably 0.5 to 10% by mass. The thickness of the positive electrode mixture layer is preferably 30 to 300 μm (per one side of the current collector).

The positive electrode having the positive electrode mixture layer can be produced in the following manner. For example, the positive electrode active material, the conductive assistant, and the binder are dispersed in water or an organic solvent such as N-methyl-2-pyrrolidone (NMP) to prepare a positive electrode mixture containing composition, e.g., in the form of slurry or paste (in this case, the binder may be dissolved in the solvent). This composition is applied to the current collector, dried, and optionally subjected to pressing such as calendering.

When the sheet-type outer case member is formed of a resin film or a laminated material of a resin film and a metal film, the resin film or a part of the laminated material may also be used as the current collector of the positive electrode. In such a case, e.g., the current collector can be provided by applying a carbon paste to the surface of the resin film or the laminated material that is to be the inner surface of the sheet-type outer case member. Alternatively, the metal layer of the laminated material can also serve as the current collector. Then, the positive electrode mixture layer or the catalyst layer can be formed on the surface of the current collector in the same manner as described above, thus producing the positive electrode. The thickness of the carbon paste layer is preferably 30 to 300 μm.

In the cell of the embodiment shown in FIG. 13, the current collector of the positive electrode is present in the low strength portion with a tear strength of 200 N or less, i.e., in the portion that is to be torn when the cell is broken. In this case, from the viewpoint of facilitating the adjustment of the tear strength of the cell to 200 N or less, it is preferable that the current collector of the positive electrode uses the resin film or a part of the laminated material of the resin film and the metal film of the sheet-type outer case member, as described above, or that the current collector of the positive electrode has a thickness of 200 μm or less.

The positive electrode is connected to a positive electrode terminal. The positive electrode terminal may be formed by connecting, e.g., aluminum foil (plate) or wire or nickel foil (plate) or wire either directly or through a lead to the current collector of the positive electrode. The positive electrode terminal in the form of foil (plate) preferably has a thickness of 50 to 500 μm. The positive electrode terminal in the form of a wire preferably has a diameter of 100 to 1500 μm.

Moreover, a portion of the current collector of the positive electrode may be exposed to the outside and used as the positive electrode terminal.

In the cell of the embodiment shown in FIG. 10, a part of the positive electrode terminal or the lead is present in the low strength portion with a tear strength of 200 N or less, i.e., in the portion that is to be torn when the cell is broken. In this case, from the viewpoint of facilitating the adjustment of the tear strength of the cell to 200 N or less, it is preferable that the portion of the positive electrode terminal to be cut (including the exposed portion of the current collector of the positive electrode that may be used as the positive electrode terminal) has a thickness of 500 μm or less or a diameter of 1500 μm or less.

To further reduce the tear strength of the low strength portion, the positive electrode terminal or the lead that is present in the portion to be cut is preferably formed of the carbon paste layer, the current collector made of metal foil, or the metal film of the outer case member.

When the sheet-type cell is an alkaline cell (primary cell or secondary cell) or a manganese cell, the negative electrode may be made of a zinc-based material (which collectively refers to both a zinc material and a zinc alloy material).

When the sheet-type cell is a nonaqueous electrolyte cell (primary cell or secondary cell), the negative electrode may have a structure in which a negative electrode mixture layer containing, e.g., a negative electrode active material and a binder is formed on one side or both sides of a current collector. Alternatively, the negative electrode may be metal foil that is to be a negative electrode active material. Further, the negative electrode may have a laminated structure of metal foil (that is to be a negative electrode active material) and a current collector.

When the sheet-type cell is a nonaqueous electrolyte primary cell, examples of the negative electrode active material include metallic lithium and a lithium alloy (lithium-aluminum alloy).

When the sheet-type cell is a nonaqueous electrolyte secondary cell, examples of the negative electrode active material include the following: metallic lithium; a lithium alloy (lithium-aluminum alloy); carbon materials such as graphite, pyrolytic carbon, coke, glassy carbon, a calcined organic polymer compound, mesophase carbon microbeads, carbon fibers, and activated carbon; alloys containing elements that can be alloyed with lithium such as Si and Sn; and oxides of Si or Sn.

The negative electrode having the negative electrode mixture layer may include any of the various binders that are described above for the positive electrode mixture layer. Moreover, the negative electrode mixture layer may contain a conductive assistant. In this case, the same conductive assistants as those for the positive electrode mixture layer may be used.

The negative electrode having the negative electrode mixture layer and the current collector can be produced in the following manner. For example, the negative electrode active material and the binder, and optionally the conductive assistant, are dispersed in water or an organic solvent such as NMP to prepare a negative electrode mixture containing composition, e.g., in the form of slurry or paste (in this case, the binder may be dissolved in the solvent). This composition is applied to the current collector, dried, and optionally subjected to pressing such as calendering.

In the composition of the negative electrode mixture layer, e.g., the amount of the negative electrode active material is preferably 70 to 99% by mass, and the content of the binder is preferably 1 to 30% by mass. When the conductive assistant is used, the content of the conductive assistant in the negative electrode mixture layer is preferably 1 to 20% by mass. The thickness of the negative electrode mixture layer is preferably 1 to 100 μm (per one side of the current collector).

The current collector of the negative electrode having the negative electrode mixture layer may be, e.g., foil, punched metal, expanded metal, or a mesh made of copper, stainless steel, nickel, titanium, or alloys thereof or may be, e.g., a sheet or mesh made of carbon. Usually, copper foil with a thickness of 5 to 30 μm is preferably used.

In the cell of the embodiment shown in FIG. 6, the current collector of the negative electrode is present in the low strength portion with a tear strength of 200 N or less, i.e., in the portion that is to be torn when the cell is broken. In this case, the negative electrode may have the same configuration as that of the above positive electrode.

When the sheet-type cell is an alkaline cell or a manganese cell, the separator of the cell may be the same as that of the above air cell.

When the sheet-type cell is a nonaqueous electrolyte cell, the separator of the cell may be preferably a polyolefin microporous film (microporous polyolefin film) or nonwoven fabric. In particular, when the cell is a secondary cell, it is preferable that the separator has the property of being able to close its pores (i.e., the shutdown function) at 80° C. or more (more preferably 100° C. or more) and 170° C. or less (more preferably 150° C. or less), and that the separator is a microporous film of polyethylene (PE) or polypropylene (PP).

In addition to the above examples, the separator may also be a microporous film or nonwoven fabric made of a heat-resistant resin such as polyimide, polyamide, aramid, or polyphenylene sulfide.

The thickness of the separator is preferably 10 to 30 μm for a microporous film and is preferably 20 to 500 μm for a nonwoven fabric.

When the sheet-type cell is an alkaline cell, the electrolyte of the cell may be an alkaline electrolyte solution. The alkaline electrolyte solution may be, e.g., an alkaline aqueous solution that includes an aqueous solution of an alkali metal hydroxide such as potassium hydroxide, sodium hydroxide, or lithium hydroxide. The alkaline electrolyte solution may also be obtained by adding zinc oxide to the alkaline aqueous solution. The concentration of the alkali metal hydroxide in the alkaline electrolyte solution is preferably 28 to 38% by mass when the alkali metal hydroxide is, e.g., potassium hydroxide. When the alkaline electrolyte solution contains zinc oxide, the concentration of zinc oxide is preferably 1.0 to 4.0% by mass.

When the sheet-type cell is a manganese cell, the electrolyte solution of the cell may be the same as that used for the electrolyte of the above air cell, but is preferably an aqueous solution of zinc chloride. In this case, the concentration of zinc chloride is preferably 10 to 40% by mass.

The electrolyte solution based on an aqueous solution and the nonaqueous electrolyte solution may be gelled (to form a gel electrolyte) using a gelling agent such as a known polymer.

There may be some cases where the electrolyte leaks to the outside due to the breakage of the sheet-type cell. In view of this, the sheet-type cell is more preferably an alkaline cell, a manganese cell, or an air cell, since these cells use an electrolyte solution containing water as a solvent (i.e., an aqueous solution of electrolyte) and thus have higher safety.

To suppress the leakage of the electrolyte solution to the outside due to the breakage of the sheet-type cell, it is more preferable that the gel electrolyte solution (gel electrolyte) is used regardless of the type of the cell, and that the low strength portion with a tear strength of 200 N or less is present in only the sealed portion of the sheet-type outer case (i.e., the conductive connection between the positive electrode or the negative electrode and the connection terminal can be interrupted by tearing the sealed portion of the sheet-type outer case), as shown in FIGS. 10, 12, and 16.

If the sheet-type cell is too thick, particularly when the sheet-type cell is torn so that the power generation elements are divided into two pieces, i.e., the piece containing the positive electrode terminal and the piece containing the negative electrode terminal, as shown in FIG. 13, it may be difficult to control the overall tear strength to be 200 N or less even though the individual tear strengths of the positive electrode, the negative electrode, the separator, and the outer case have been adjusted. Thus, the sheet-type cell cannot be easily torn by hand. For this reason, the thickness of the sheet-type cell (i.e., the length of t in FIG. 11) is preferably 1 mm or less.

On the other hand, as shown in FIGS. 10, 12, and 16, when the low strength portion with a tear strength of 200 N or less is present in the sealed portion where at least one of the positive electrode terminal and the negative electrode terminal is provided, the thickness of the sheet-type cell is not particularly limited and may be determined in accordance with, e.g., the intended use of the cell. Usually, the thickness of the sheet-type cell is preferably 1 mm or less to facilitate the incineration of the cell when it is disposed of as waste.

The lower limit of the thickness of the sheet-type cell is not particularly limited regardless of the position of the low strength portion with a tear strength of 200 N or less, and usually may be 0.2 mm or more to maintain a predetermined amount of capacity.

The sheet-type cell of the present application can easily be broken and disposed of after use. Therefore, the sheet-type cell is particularly suitable for applications that require disposal by the user. Moreover, the sheet-type cell is applicable to various applications that use a variety of cells.

EXAMPLES

Hereinafter, the sheet-type cell of the present application will be described in detail by way of examples. However, the sheet-type cell of the present application is not limited to the following examples.

Example 1

Positive Electrode

First, 75 parts by mass of Ketjenblack, 25 parts by mass of PTFE, and water were mixed and rolled between rotating rolls to form a sheet for a catalyst layer. This sheet was pressure bonded to a carbon sheet (current collector) with a thickness of 100 m, and then dried. Next, the resulting sheet was punched into a shape having the catalyst layer that was 30 mm×30 mm in size and an exposed portion of the current collector at one end. The exposed portion of the current collector was used as a lead and a positive electrode terminal. Thus, a positive electrode (air electrode) with a total thickness of 200 μm was produced.

<Negative Electrode>

First, 95 parts by mass of zinc alloy particles containing additional elements of In: 0.05%, Bi: 0.04%, and Al: 0.001% and 5 parts by mass of CMC were dispersed in water to form a negative electrode paste. Then, the negative electrode paste was applied to a carbon sheet with a thickness of 100 μm so that the thickness of the paste after drying was 100 μm. Subsequently, the negative electrode paste was dried, and the resulting sheet was punched into a shape having the layer that contained the zinc alloy particles and CMC and was 30 mm×30 mm in size, and an exposed portion of the current collector at one end. The exposed portion of the current collector was used as a lead and a negative electrode terminal. Thus, a negative electrode with a total thickness of 200 μm was produced.

<Electrolyte solution>

An electrolyte solution was a sodium chloride aqueous solution (pH=6) with a concentration of 20% by mass, containing an acrylic resin thickening agent with a concentration of 1% by mass.

<Separator>

A separator was produced by forming two graft films (thickness: 30 μm) on both sides of a cellophane film (thickness: 20 μm), on top of which vinylon-rayon mixed paper (thickness: 100 μm) was further formed. The graft films were composed of a graft copolymer obtained by graft copolymerization of acrylic acid with a polyethylene main chain.

<Water Repellent Membrane>

A water repellent membrane was a polyethylene sheet with a thickness of 200 μm.

<Cell Assembly>

Two 5 cm×5 cm aluminum laminated films were used as sheet-type outer case members. Each of the aluminum laminated films had a structure in which a PET film was provided on the outer surface of aluminum foil, and a polypropylene film (heat-sealing resin layer) was provided on the inner surface of the aluminum foil.

As shown in FIG. 1, nine air holes, each having a diameter of 1 mm, were regularly formed in one of the aluminum laminated films. The air holes were spaced at regular intervals of 9 mm (length)×9 mm (width) (i.e., the center-to-center distance of adjacent air holes: 10 mm). Then, the water repellent membrane was thermally fused to the inner surface of this aluminum laminated film with a hot-melt adhesive.

Moreover, the other aluminum laminated film (which did not have a water repellent membrane), the negative electrode, the separator, the positive electrode, and the aluminum laminated film having the water repellent membrane were formed in this order. Then, three sides of the two aluminum laminated films (other than the side from which the exposed portions of the current collectors of the positive electrode and the negative electrode were to be drawn) were thermally fused to each other, thus providing a bag-like outer case. After the electrolyte solution was injected through the opening of the bag-like outer case, the opening was sealed by thermal fusion, and consequently a sheet-type air cell was obtained.

To improve the sealing properties of the sealed portion (thermally fused portion) between the outer case members and the exposed portions (leads) of the current collectors of the positive electrode and the negative electrode, a polypropylene tape was previously attached to each of the leads, and then the thermal fusion process was performed.

Next, a starting point of a low strength portion with a tear strength of 200 N or less was formed by making a 2 mm long cut with a knife in the sealed portion of the sheet-type air cell at the position shown in FIG. 1, where the exposed portions (external terminals) of the current collectors of the positive electrode and the negative electrode were drawn.

Example 2

A sheet-type air cell was produced in the same manner as Example 1 except that a starting point of a low strength portion with a tear strength of 200 N or less was formed by making a 2 mm long cut with a knife in the sealed portion of the sheet-type air cell at the position between two terminals (see FIG. 13), i.e., between the exposed portion of the current collector of the positive electrode (the positive electrode terminal) and the exposed portion of the current collector of the negative electrode (the negative electrode terminal).

Example 3

A sheet-type air cell was produced in the same manner as Example 1 except that the current collectors of the positive electrode and the negative electrode were changed to nickel foil with a thickness of 100 μm.

Comparative Example 1

A sheet-type air cell was produced in the same manner as Example 1 except that no cut was made in the sealed portion of the sheet-type outer case.

Comparative Example 2

A sheet-type air cell was produced in the same manner as Example 1 except that a nickel plate with a thickness of 1000 m was connected to each of the current collectors of the positive electrode and the negative electrode and was used as a lead and an external terminal.

Using the sheet-type air cells of Examples 1 to 3 and Comparative Examples 1, 2, the tear strength was measured by the method as described above, and a manual tearing test was performed to evaluate the hand tearability (i.e., whether each cell can be torn by hand). Specifically, the tear strength measurement and the manual tearing test were performed on the cells of Examples 1 to 3 and Comparative Example 2 so as to tear each of the cells straight from the cut in the sealed portion toward the opposite sealed portion. The cell of Comparative Example 1 did not have a cut in the sealed portion. Therefore, the tear strength measurement and the manual tearing test were performed on the cell of Comparative Example 1 in the same positions as those of the cell of Example 1 or the like and the cell of Example 2.

Table 2 shows the evaluation results. In Table 2, Comparative Example 1 is represented by "A" and "B": "A" indicates the results of the tear strength measurement and the manual tearing test in the same position as that of the cell of Example 1 or the like; and "B" indicates the results of the tear strength measurement and the manual tearing test in the same position as that of the cell of Example 2.

TABLE 2

|  |  | Tear strength (N) | Hand tearability |
|---|---|---|---|
| Example 1 |  | 6 | tearable |
| Example 2 |  | 20 | tearable |
| Example 3 |  | 87 | tearable |
| Comparative Example 1 | A | >200 | non tearable |
|  | B | >200 | non tearable |
| Comparative Example 2 |  | >200 | non tearable |

As shown in Table 2, the sheet-type air cells of Examples 1 to 3 have low strength portions with a tear strength of 200 N or less, and thus can be torn by hand at their respective low strength portions.

On the other hand, the cell of Comparative Example 1, in which no cut is formed in the sealed portion of the sheet-type outer case, and the cell of Comparative Example 2, in which the external terminals of the positive electrode and the negative electrode are thick nickel plates, do not have a low strength portion with a tear strength of 200 N or less, and thus cannot be torn by hand.

As described above, the sheet-type cell of the present application has a low strength portion with a tear strength of 200 N or less as the cutting facilitating member so as to be able to (1) interrupt at least one of the conductive connections between the positive electrode and the positive electrode terminal and between the negative electrode and the negative electrode terminal to supply power from the cell to the outside or to (2) separate the power generation elements into two parts. In addition to the low strength portion, the sheet-type cell may have a cutting start portion, a cut tape, or a cutting portion as the cutting facilitating member that allows the cell to be cut with a force of 200 N or less. Therefore, e.g., adults can tear the sheet-type cell into two pieces by hand at the cutting facilitating member, or can cut a part of the outer case at the cutting facilitating member so that the cell is divided into two parts that are not electrically connected to each other.

Thus, the sheet-type cell of the present application can easily be broken and substantially lose its function, e.g., when it no longer needs to be used. Consequently, the sheet-type cell can be disposed of easily and safely.

INDUSTRIAL APPLICABILITY

The wearable patch of the present disclosure has the cutting facilitating member that allows a predetermined portion of the wearable patch to be cut with a force of 200 N or less. Thus, the operation of the wearable patch after use can be stopped easily and reliably.

The sheet-type cell of the present disclosure has the cutting facilitating member that allows a predetermined portion of the sheet-type cell to be cut with a force of 200 N or less. Thus, the power supply from the sheet-type cell to the outside after use can be interrupted easily and reliably.

Therefore, the present disclosure is particularly useful mainly in the medical field because the used wearable patch or sheet-type cell can be disposed of safely even in the fields of medical care and personal use.

DESCRIPTION OF REFERENCE NUMERALS

10 Sheet-type air cell (cell)
20 Drive circuit unit
30 Base
50 Functional element
60 Adhesive layer
70 Cutting start portion (cutting facilitating member)
71 Cut (cutting start portion)
100 Wearable patch
520 Positive electrode
521 Positive electrode terminal
530 Negative electrode
531 Negative electrode terminal
540 Separator
560 (Sheet-type) outer case
570 Cutting start portion (cutting facilitating member)
571 Cut (cutting start portion)
572 Low strength portion

The invention claimed is:

1. A wearable patch that is worn on the body, comprising a functional element;
a drive circuit unit that operates the functional element; and
a cell as a power source,
wherein a cutting facilitating member is formed to allow a predetermined portion of the wearable patch to be cut with a force of 200 N or less so that power supply from the cell to the drive circuit unit is interrupted.

2. The wearable patch according to claim 1, comprising a conductive path that connects the cell and the drive circuit unit,
wherein the conductive path can be cut by the cutting facilitating member.

3. The wearable patch according to claim 1, wherein the cell comprises power generation elements, including a positive electrode and a negative electrode, that are placed inside a sheet-type outer case, and a positive electrode terminal and a negative electrode terminal that are connected to the positive electrode and the negative electrode, respectively, to feed power generated by the power generation elements to the outside,
wherein at least one of the positive electrode terminal and the negative electrode terminal can be cut by the cutting facilitating member.

4. The wearable patch according to claim 1, wherein the cell is a sheet-type cell that comprises power generation elements, including a sheet-type positive electrode and a sheet-type negative electrode, that are placed inside a sheet-type outer case, and
wherein the power generation elements can be cut by the cutting facilitating member.

5. The wearable patch according to claim 1, having a cutting start portion as the cutting facilitating member,
wherein the cutting start portion serves as a starting point for cutting.

6. The wearable patch according to claim 5, wherein the cutting start portion includes a cut formed in an edge of the wearable patch.

7. The wearable patch according to claim 1, having a cut tape as the cutting facilitating member,
   wherein the cut tape is provided so that the predetermined portion can be cut by pulling up one end of the cut tape that is located at an edge of the wearable patch.

8. The wearable patch according to claim 1, having a cutting portion as the cutting facilitating member,
   wherein the cutting portion can easily be cut compared to other portions.

9. The wearable patch according to claim 8, wherein the cutting portion includes perforations.

10. A sheet-type cell comprising:
    power generation elements, including a sheet-type positive electrode and a sheet-type negative electrode, that are sealed in a sheet-type outer case,
    wherein a cutting facilitating member is formed to allow a predetermined portion of the sheet-type cell to be cut with a force of 200 N or less so that power supply from the cell to the outside is interrupted.

11. The sheet-type cell according to claim 10, comprising a positive electrode terminal and a negative electrode terminal that are connected to the positive electrode and the negative electrode, respectively, to feed power generated by the power generation elements to the outside,
    wherein at least one of the positive electrode terminal and the negative electrode terminal can be cut by the cutting facilitating member.

12. The sheet-type cell according to claim 10, wherein the power generation elements can be cut by the cutting facilitating member.

13. The sheet-type cell according to claim 10, having a cutting start portion as the cutting facilitating member,
    wherein the cutting start portion serves as a starting point for cutting.

14. The sheet-type cell according to claim 13, wherein the cutting start portion includes a cut formed in an edge of the sheet-type cell.

15. The sheet-type cell according to claim 10, having a cut tape as the cutting facilitating member,
    wherein the cut tape is provided so that the predetermined portion can be cut by pulling up one end of the cut tape that is located at an edge of the sheet-type cell.

16. The sheet-type cell according to claim 10, having a cutting portion as the cutting facilitating member,
    wherein the cutting portion can easily be cut compared to other portions.

17. The sheet-type cell according to claim 16, wherein the cutting portion includes perforations.

\* \* \* \* \*